US010271819B2

(12) United States Patent
Frenz et al.

(10) Patent No.: US 10,271,819 B2
(45) Date of Patent: Apr. 30, 2019

(54) COMPUTED ULTRASOUND TOMOGRAPHY IN ECHO MODE (CUTE) FOR IMAGING SPEED OF SOUND USING PULSE-ECHO SONOGRAPHY

(71) Applicant: UNIVERSITAT BERN, Bern (CH)

(72) Inventors: Martin Frenz, Munsingen (CH); Michael Jaeger, Bern (CH)

(73) Assignee: UNIVERSITAT BERN, Bern (CH)

( * ) Notice: Subject to any disclaimer, the term of this patent is extended or adjusted under 35 U.S.C. 154(b) by 215 days.

(21) Appl. No.: 15/104,992

(22) PCT Filed: Dec. 16, 2014

(86) PCT No.: PCT/EP2014/078011
§ 371 (c)(1),
(2) Date: Jun. 16, 2016

(87) PCT Pub. No.: WO2015/091519
PCT Pub. Date: Jun. 25, 2015

(65) Prior Publication Data
US 2016/0317121 A1  Nov. 3, 2016

(30) Foreign Application Priority Data

Dec. 16, 2013  (EP) .................................... 13197566

(51) Int. Cl.
*A61B 8/14*  (2006.01)
*A61B 8/08*  (2006.01)
(Continued)

(52) U.S. Cl.
CPC .................. *A61B 8/14* (2013.01); *A61B 8/08* (2013.01); *A61B 8/085* (2013.01); *A61B 8/48* (2013.01);
(Continued)

(58) Field of Classification Search
CPC .. A61B 8/14; A61B 8/085; A61B 8/08; A61B 8/5269; A61B 8/5223; A61B 8/48;
(Continued)

(56) References Cited

U.S. PATENT DOCUMENTS 7,229,411 B2 * 6/2007 Slayton .................... A61B 5/01
600/437
2007/0016038 A1 * 1/2007 Lynch .................. A61B 8/0875
600/438

(Continued)

*Primary Examiner* — Sanjay Cattungal
(74) *Attorney, Agent, or Firm* — JMB Davis Ben-David

(57) ABSTRACT

The invention relates to a method for determining and particularly imaging sound speed in an object by means of pulse-echo ultrasound, comprising the steps of: transmitting by means of an ultrasound probe (1) at least a first ultrasound pulse (10) in a first direction ($\varphi_0$) and a second ultrasound pulse (20) in a different second direction ($\varphi$) into an object (O) to be imaged, so that said first ultrasound pulse (10) is backscattered in said object towards said ultrasound probe in the form of first ultrasound pulse echoes (11), and so that said second ultrasound pulse (20) is backscattered in said object towards said ultrasound probe in the form of second ultrasound pulse echoes (21), detecting said backscattered first ultrasound pulse echoes (11) and said backscattered second ultrasound pulse echoes (21) with said ultrasound probe (1), reconstructing from said detected backscattered first ultrasound pulse echoes (11) a first image of first local echoes (5) and from said detected backscattered second ultrasound pulse echoes (21) a second image of second local echoes (7), wherein said images lie in an image plane spanned by said directions ($\varphi_0$, $\varphi$), determining from said reconstructed images the respective resulting local echo phase shift $\Delta\tau(x, z, \varphi, \varphi_0)$ corresponding to the difference in echo time (t) between the respective first local echo and the corresponding second local echo relative to the case of an assumed constant sound speed, and determining the local sound speed $c(x, z)$ in said object for at least a region of said (Continued)

Figure 1:
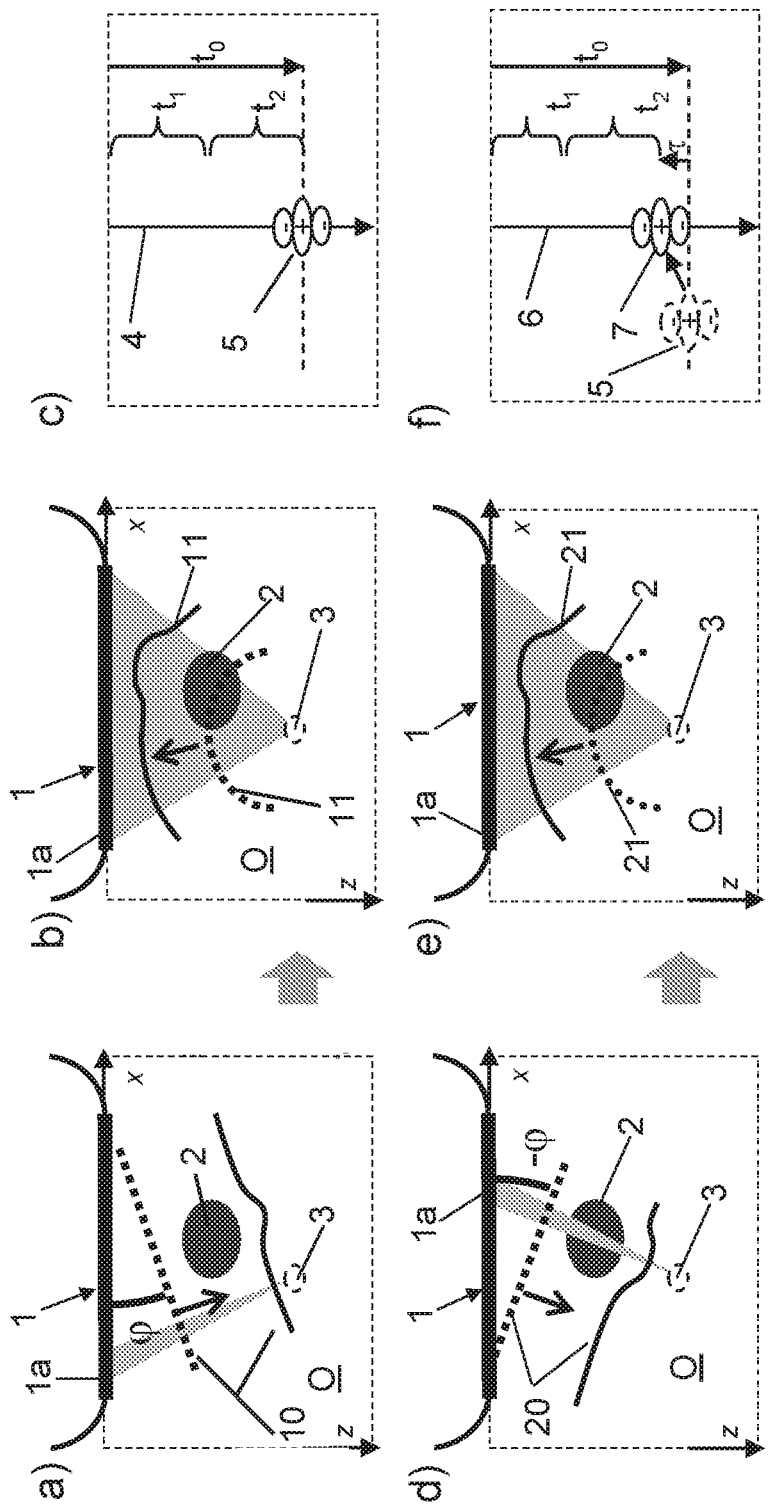

image plane in said object from said local echo phase shift $\Delta\tau(x, z, \varphi, \varphi_0)$. Further, the invention relates to a corresponding computer program and a system.

14 Claims, 14 Drawing Sheets

(51) Int. Cl.
  *G01S 7/52* (2006.01)
  *G01S 15/89* (2006.01)
  *G01H 5/00* (2006.01)
(52) U.S. Cl.
  CPC .......... *A61B 8/5223* (2013.01); *A61B 8/5269* (2013.01); *G01S 7/52036* (2013.01); *G01S 7/52049* (2013.01); *G01S 7/52071* (2013.01); *G01S 15/8977* (2013.01); *G01H 5/00* (2013.01); *G01S 7/52077* (2013.01)
(58) Field of Classification Search
  CPC ............. G01S 7/52071; G01S 7/52049; G01S 15/8977; G01S 7/52036; G01S 7/52077; G01H 5/00
  USPC .................................................. 600/437–469
  See application file for complete search history.

(56) References Cited

U.S. PATENT DOCUMENTS

| | | | |
|---|---|---|---|
| 2009/0182230 A1* | 7/2009 | Liu | A61B 5/01 600/439 |
| 2013/0251222 A1* | 9/2013 | Huang | A61B 8/13 382/131 |

* cited by examiner

COMPUTED ULTRASOUND TOMOGRAPHY IN ECHO MODE (CUTE) FOR IMAGING SPEED OF SOUND USING PULSE-ECHO SONOGRAPHY

CROSS-REFERENCE TO RELATED APPLICATIONS

This is the U.S. National Stage of International Application No. PCT/EP2014/078011, filed Dec. 16, 2014, which was published in English under PCT Article 21(2), and which in turn claims the benefit of EP Patent Application No. 13197566.6, filed Dec. 16, 2013.

SPECIFICATION

The invention relates to a method for determining and particularly imaging sound speed in an object by means of pulse-echo ultrasound. Further, the invention relates to a computer program as well as to a system for carrying out the method according to the invention.

Difficulties in differential diagnosis using ultrasound have motivated the search for novel ultrasound-based modalities to develop ultrasound to a multi-modal device. One promising candidate is the speed of sound which differs not only between different tissue types but also between healthy and diseased tissue. Transmission ultrasound tomography has the ability of imaging speed of sound spatially resolved but is limited to the acoustically transparent breast. Herein, a novel method which allows speed-of-sound imaging with high contrast and spatial resolution using conventional pulse-echo ultrasound is presented. This will allow much wider clinical applicability and the combination with state-of-the art diagnostic ultrasound in a multi-modal approach. Advantageously, a contrast resolution of better than 0.8% of average sound speed at a resolution of 1 mm can be achieved with the method according to the invention.

Diagnostic imaging is an integral part of today's clinical practise. Out of the various established modalities, ultrasound (US) is low-cost, non-ionizing, and provides the patient short, comfortable sessions. Real-time and free-hand operation makes it easy to quickly access different parts of the body, and the technical development of the last decade provides one with strongly miniaturised, laptop-sized US-systems that can be versatilely employed at the point-of-care and emergency level. Unfortunately, these favourable features of conventional US in comparison to other modalities are often counterweighed by unspecific contrast for certain disease types resulting in difficulties in differential diagnosis.

Much effort has therefore been put in improving the diagnostic accuracy of US while maintaining the benefits of real-time operability and flexibility, by comprising new modalities that are based on the same equipment but complement classical gray-scale B-mode US with additional structural and functional information.

Speed and attenuation of ultrasound can reflect disease-related changes in tissue composition. A lot of effort has therefore been put in developing methods for imaging those parameters in a spatially resolved way, to provide a novel diagnostic modality in combination with US. To this end, imaging of speed and attenuation of ultrasound has been demonstrated in ultrasound computed tomography (UCT) of the breast. The breast is located in a water tank inside an annular array of several hundred ultrasound transducer elements, and the time delay and amplitude of ultrasound when propagating through the breast from various directions allows tomographic reconstruction of sound speed and attenuation in a way similar to X-ray computed tomography (CT). UCT allowed the differentiation between malignant and benign tissue in vivo, and the differentiation between malignant and benign tissue with sensitivity around 80% and specificity around 90% [1] in vitro.

Sound speed contrast as a novel diagnostic modality will be clinically most successful if employed in combination with conventional US with its real-time operability and flexibility using hand-held probes. Unfortunately, UCT is based on ultrasound transmission through the tissue and can only be employed with acoustically transparent tissues such as the breast, and the strongly specialised and rigid setup requires standalone dedicated equipment. Therefore, several approaches that would allow sound speed measurement in reflection mode using the pulse-echo signal as opposed to ultrasound transmission were proposed in the past: (i) Assuming a wrong sound speed for B-mode image reconstruction results in blurring of point-like structures. Conversely, iterative optimisation of spatial resolution via tuning the sound speed parameter yields a measure of true sound speed. (ii) Assuming a wrong sound speed for image reconstruction results in geometric distortions of the B-mode image. Conversely, the misregistration of B-mode images that results when scanning the tissue from different directions can be used to gain information about average sound speed within large tissue regions. These approaches allowed determination of sound speed with rather low spatial resolution. (iii) A more direct method for measuring sound speed in a spatially resolved way was the crossed-beam or the beam-tracking method. Based on scanning the tissue with acoustic beams with intersecting axes, one for transmission and one for reception, the time of flight of acoustic power coupled from one into the other beam allowed the measurement of sound speed along the propagation path. This principle was implemented for clinical imaging on a linear probe with shifting transmit and receive apertures, and a spatial resolution of 10 mm for detecting an inclusion with 1% sound speed contrast was reported in simulations.

Based on the above, the problem underlying the present invention is to provide for a method for determining and particularly imaging sound speed in an object by means of pulse-echo ultrasound as well as a computer program and a system for carrying out the method according to the invention.

This problem is solved by a method having the features of claim 1. Preferred embodiments are stated in the corresponding sub claims.

According to claim 1 the method according to the invention comprises the steps of:

transmitting by means of an ultrasound probe at least a first ultrasound pulse in a first direction and a second ultrasound pulse in a different second direction into an object to be imaged, so that said first ultrasound pulse is backscattered in said object towards said ultrasound probe in the form of first ultrasound pulse echoes, and so that said second ultrasound pulse is backscattered in said object towards said ultrasound probe in the form of second ultrasound pulse echoes, detecting said backscattered first ultrasound pulse echoes and said backscattered second ultrasound pulse echoes with said ultrasound probe, reconstructing from said detected backscattered first ultrasound pulse echoes a first image of first local echoes and from said detected backscattered second ultrasound pulse echoes a second image of second local echoes, wherein said images lie in an image plane spanned by said directions, determining from said reconstructed images the respective resulting local echo phase shift $\Delta\tau(x,z,\varphi,\varphi_0)$ at locations (x,z) in said image plane between the respective first local echoes and the corresponding second local echoes, which phase shift corresponds to the difference in echo time (t) between the respective first local echoes and the corresponding second local echoes compared to the case of an assumed constant sound speed in said object, and determining the local sound speed c(x,z) in said object for at least a region of said image plane in said object from said local echo phase shifts $\Delta\tau(x,z,\varphi,\varphi_0)$.

Preferably, apart from the necessity to acquire ultrasound images, all method steps are preferably carried out automatically, e.g. by using a computer/computer program.

The first direction (also denoted Tx angle) is specified by a first angle $\varphi_0$ which is enclosed by the first direction and a z-axis that lies in said image plane and extends in a depth direction of the object to be imaged, and wherein said second direction (also denoted Tx angle) is specified by an angle $\varphi$ which is enclosed by the second direction and said z-axis.

Here, preferably, the local echo phase shift $\Delta\tau(x,z,\varphi,\varphi_0)$ is a map containing the respective local echo phase shifts between the respective first local echoes and the associated second local echoes from ultrasound scatterers at positions (x,z) in the image plane. The respective local echo phase shift is the change of depth z at which a respective first local echo and an associated second echo, scattered at the same scatterer, are reconstructed assuming a homogeneous sound speed $c_0$. The depth z at which a local echo is reconstructed accounts both for the time the incident (first or second) ultrasound pulse needs to reach the scatterer and the time the respective (first or second) backscattered ultrasound pulse echo needs to get back to the probe. Deviations of sound speed from $c_0$ cause the echoes to be reconstructed at depths z in the object different from the true depth $z_0$. Since the time the backscattered ultrasound pulse echoes need to get back to the probe is independent from the direction of the transmitted ultrasound pulse, the local echo phase shift is only determined by the deviation of the arrival times of said incident first or second ultrasound pulses at the scatterer compared to the arrival times in case where the assumption of the homogeneous sound speed $c_0$ would hold true.

Such a phase shift may result as follows: When an incident e.g. plane transient (first ultrasound pulse) propagates through the tissue with sound speed $c_0$ such that it is not influenced by a spatially confined sound speed contrast region (region with e.g. higher sound speed $c > c_0$) in the object, a part of the wave may be backscattered by a hypothetical acoustic point scatterer. The backscattered spherical sound wave is detected using the full probe aperture, irrespective of the Tx angle characterizing said first direction. When the Tx angle $\varphi$ now changes (second direction), the part of the Tx wave which arrives at the scatterer may now transit the contrast region, and the average sound speed along the propagation path is larger than $c_0$, so that it arrives earlier at the scatterer than in the case of constant sound speed $c_0$. The echo time t can thus be expressed as $t=t_0+\tau(p)$, where $\tau(p)$ is the additional local echo phase caused by the sound speed contrast, relative to the hypothetical case of zero contrast (constant sound speed $c_0$ everywhere). This phase reflects the deviation of the sound speed from the reference value $c_0$, accumulated along the acoustic line of propagation from the probe to the acoustic scatterer. When scanning the Tx angle, tracking the echo phase therefore provides a means of probing sound speed along lines of different direction. When changing the Tx angle $\varphi$, only the transmit part of the ultrasound propagation path from the probe to the scatterer changes, whereas the receive part remains the same.

Preferably, the ultrasound probe used in the method according to the invention comprises a plurality of ultrasound transducers (also denoted as elements of the probe), particularly arranged in a linear array, so that 2D ultrasound images can be acquired with the probe. Preferably, the probe is a handheld probe.

The method according to the invention is also denoted as computed ultrasound tomography in echo mode (CUTE) and shows great potential for real-time tomographic imaging of sound speed using the pulse-echo signal acquired by particularly handheld probes, with both contrast (better than 1% of total sound speed) and resolution (in the range of one millimeter) suitable for diagnostic imaging. The present method employs the phase of local echoes as a measure of sound speed along lines of propagation between the ultrasound probe and the echo producing structures. When steering the direction of the transmit beam, the phase of the echoes produced by local scatterers allows the tomographic reconstruction of sound speed similar to UCT but without the need for ultrasound detection at the opposite side of the tissue. This makes CUTE suitable also to tissue where bones obstruct ultrasound transmission and which is therefore not accessible to UCT, and opens a much larger field of application.

Further, preferably, less than 10, 9, 8, 7, 6, 5, or 3 different directions are used for the incident ultrasound pulses. Particularly, merely said two different directions are employed.

According to a preferred embodiment of the present invention, a sound speed image is generated from the local sound speed c(x,z), wherein particularly said sound speed image is visualized, particularly displayed on a display means. Particularly, the sound speed image is a digital image comprising pixels having a pixel value corresponding to the respective local sound speed.

According to a preferred embodiment of the present invention, said determining of the local sound speed c(x,z), said generating of said sound speed image from the local sound speed c(x,z), and/or said visualizing is conducted in real-time.

The images of the local echoes are reconstructed from the detected backscattered pulse echoes which are received by the probe. Each element of the array probe preferably detects a time-resolved radio frequency (RF) signal. Preferably, the RF signals of the different elements are combined to synthetically focus the probe along different lines of sight in a dynamic way. The resulting synthetically focused RF signal for each line of sight is a so called A-line. The A-lines comprise the local echoes that come back versus time, and the time-axis is coded into spatial coordinates. Typically, an A-line points into the depth direction z perpendicular to the line of array elements which defines the axis of lateral position x. Synthetically focusing to an image point (x,z) located on the A-line starting at the lateral position x is typically performed in the following way: The time $t_1(x,z)$ of arrival of the transmitted ultrasound wave at position (x,z) (transmit time delay) is calculated based on an assumed constant speed of sound equal to the average speed of sound of soft tissue, 1540 m/s. Then the time delays $t_2(x,z,x')$ of propagation of the echo from position (x,z) to the different array elements located at positions (x',z=0) (receive time delays) are calculated based on the assumed speed of sound. The amplitude u(x,z) at depth z on the A-line at position x is then calculated as the sum of the RF signals $s(x'_i, t)$ detected by the $i^{th}$ elements:

$$u(x, z) = \sum_{i=1}^{N} s(x'_i, t_1(x, z) + t_2(x, z, x'_i))$$

Each image consists of a number of A-lines with different lateral position x. The number of A-lines may correspond to the number of ultrasound transducers of the ultrasound probe, but can also be chosen independently. Such a reconstructed image is herein also denoted as RF image because it contains RF amplitude data. For visual presentation of the image, the latter may undergo at least one post processing step, preferably one or several of the following post processing steps: a band pass filtering, an envelope calculation, a logarithmic compression, and eventually a low pass filtering. Preferably, these steps are carried out in the stated order. The resulting image shall be called the postprocessed image. When converted to grey scale this corresponds to the known B-mode representation, i.e. the brighter the pixel value the stronger the echo at this position.

The sound speed can be reconstructed either from the RF image or from the postprocessed image. Preferably, the RF image is used. This is preferably a digital image comprising pixels (x,z), wherein a pixel value is assigned to each pixel which is the RF amplitude of the respective A-line that comprises the location of this pixel, evaluated at the location of this pixel.

According to a preferred embodiment of the present invention, the A-line that contains a respective first local echo located at position (x,z) is modeled as respective first amplitude-modulated complex sinusoidal carrier, and the A-line that contains the associated second local echo is modeled as second amplitude-modulated complex sinusoidal carrier.

Preferably, the respective local echo phase shift $\Delta\tau(x,z,\varphi,\varphi_0)$ is determined as the phase shift between the respective first carrier and the corresponding second carrier. This provides for a stable estimation of the local echo phase shifts since the frequency of the carriers is typically larger than that of the envelope, i.e., the envelope varies considerably less over a certain period of time than the carriers.

According to a preferred embodiment of the present invention the respective local echo phase shift $\Delta\tau(x,z,\varphi,\varphi_0)$ may be determined by: calculating a first Hilbert transform of a respective first RF image which was obtained with a respective first TX angle (i.e. direction), and a corresponding second Hilbert transform of a respective second RF image obtained with a respective second TX angle (i.e. direction), particularly in a direction of the A-lines, respectively, calculating a pointwise product (the pointwise product (f·g): X→Y is defined by (f·g)(x)=f(x)·g(x)) between each first Hilbert transform and the complex conjugate of the corresponding second Hilbert transform, calculating a convolution of the point-wise absolute magnitude of the point-wise product with a convolution kernel yielding a local average echo power, determining a pointwise quotient (i.e. (f/g): X→Y defined by (f/g)(x)=f(x)/g(x)) between the point-wise product and its associated average local echo power, calculating a complex local average of the point-wise quotient by calculating a convolution of the point-wise quotient with a convolution kernel, and determining the local echo phase shift $\Delta\tau(x,z,\varphi,\varphi_0)$ as the argument of said complex local average (in polar form) of the point-wise quotient. Preferred convolution kernels are 2D boxcar windows, preferably with diameters that correspond to 1 mm in lateral (x) direction and 3 mm in axial (z) direction. Other window functions that are typically used in signal processing (Hanning, Hamming etc.) may also be used. Other sizes of the window function may also be used.

According to a preferred embodiment of the present invention the discrete Fourier Transform $\Delta\tau(k_x,k_z,\varphi,\varphi_0)$ of the local echo phase shift $\Delta\tau(x,z,\varphi,\varphi_0)$ is automatically calculated for determining the local sound speed c(x,z).

According to a preferred embodiment of the present invention the local sound speed c(x,z) in said object is automatically determined from the Fourier transformed local echo phase shift $\Delta\tau(k_x, k_z,\varphi,\varphi_0)$ using the relation $$\sigma(k_x,k_z)=T_{inv}(k_x',k_z',k_x,k_z,\varphi,\varphi_0)\cdot\Delta\tau(k_x',k_z',\varphi,\varphi_0),$$

(or a relation equivalent thereto) wherein $\sigma(k_x, k_z)$ is the discrete Fourier transform of the slowness $\sigma(x,z)$, wherein the slowness $\sigma(x,z)+\sigma_0$ is the reciprocal of the sound speed c(x,z), and $T_{inv}$ is a matrix (here, $\sigma_0$ is a homogeneous reference slowness of the object)

Preferably, the local sound speed is automatically obtained from the reciprocal of said sound speed.

Preferably, said matrix $T_{inv}$ is an inverse matrix of the matrix $$T(k_x',k_z',k_x,k_z,\varphi,\varphi_0)=M(k_x',k_z',k_x,k_z,\varphi)-M(k_x',k_z',k_x,k_z,\varphi),$$ M having the components $M_{k',k}(\varphi)$ with:

$$M_{k',k}(\varphi) = \frac{\sqrt{1+\tan^2\varphi}}{i(k_x\tan\varphi+k_z)} \cdot X \cdot \delta(k_x-k_x') \cdot ...$$

$$\left\{Z\cdot\delta(k_z-k_z') + \frac{1}{i(k_x\tan\varphi+k_z')}\{\exp[-i(k_x\tan\varphi+k_z')Z]-1\}\right\}$$

wherein the image (region) has dimensions X (laterally) and Z (axially in the depth direction).

According to a preferred embodiment of the present invention said matrix $T_{inv}$ is the Tikhonov pseudo-inverse matrix:

$$T^{-1}\dot{=}(T^*T+\Gamma^*\Gamma)^{-1}T^*,$$

wherein * denotes the complex transpose, and wherein particularly $\Gamma$ is a regularizing term. According to an embodiment of the present invention, the regularising term $\Gamma$ is the identity matrix multiplied with a real-valued regularization parameter $\gamma$.

For instance, for determining the local sound speed in the image plane, the matrix T may be obtained from $M_{k',k}(\varphi)$ (e.g. as stated above). Further, the inverse of T may be calculated as the Tikhonov pseudo-inverse $T^{-1}$ (e.g. as stated above).

Preferably, the reconstruction of the sound speed comprises following steps:

Determination the local echo phase shift $\Delta\tau(\varphi,\varphi_0,x,z)$ (see e.g. above), Carrying out the Fourier transform $\Delta\tau(x,z,\varphi,\varphi_0)$ to $\Delta\tau(k_x, k_z,\varphi,\varphi_0)$, Carrying out the matrix operation:

$$\sigma(k_x,k_z,\varphi,\varphi_0)=\Sigma_{k_x',k_z'}T_{inv}(k_x',k_z',k_x,k_z,\varphi,\varphi_0)\cdot\Delta\tau(k_x',k_z',\varphi,\varphi_0)$$

Performing the inverse Fourier transform $\sigma(k_x,k_z,\varphi,\varphi_0)$ to $\sigma(x,z,\varphi,\varphi_0)$.

Then, the local sound speed may be obtained from the reciprocal of $\sigma_0+\sigma(x,z)$.

Preferably, according to a further embodiment of the present invention, the slowness distribution $\sigma(x,z)$ is determined from the local echo phase shift $\Delta\tau(x,z,\varphi,\varphi_0)$ in an iterative manner, which particularly allows one to compensate for the effect of acoustic refraction.

In this regard, particularly straight ray sound propagation is in a first iteration assumed for image reconstruction. Acoustic refraction is the bending of sound rays, caused by a spatial gradient of the slowness distribution. This results in image distortion and thus errors in the echo phase shift and in the estimated slowness distribution.

Preferably, in a first iteration, a constant slowness $\sigma_0$ is assumed for calculation of the transmit and receive time delays, $t_1(x,z)$ and $t_2(x,z,x')$, respectively, for reconstruction of said first image of first local echoes and said second image of second local echoes, from which a first local echo phase shift and a first estimate of the slowness distribution $\sigma$ is determined, particularly as described above.

Preferably, in a second iteration, the transmit and receive time delays $t_1(x,z)$ and $t_2(x,z,x')$ for said image reconstruction of said first image of first local echoes and said second image of second local echoes are calculated using said first estimate of the slowness distribution $\sigma(x,z)$. Particularly, this allows one to account for acoustic refraction based on the first estimate of the slowness distribution, resulting in first and second images of local echoes (second iteration) with less distortion, from which a second local echo phase shift and a second (more accurate) estimate of the slowness distribution is determined, particularly as described above. The iteration is stopped after a pre-defined number of iterations. Advantageously, with consecutive further n-th iterations, the n-th estimate of the slowness distribution converges more towards the true slowness distribution.

Further, preferably, the method according to the invention is applied to objects such as soft tissue of a human or an animal, a liver of a human or an animal, particularly showing fibrosis, cirrhosis or fatty liver disease, or a part of a human or animal body comprising a tumor.

Thus, the invention can be used in the framework of diagnosis of the composition of state of soft tissues in humans or animals, e.g. for diagnosis and staging of diseases such as cancer, liver fibrosis or cirrhosis, fatty liver disease, as well as for the differential diagnosis between different tumor types, and other diseases.

According to a further embodiment of the present invention the reconstructed distribution of sound speed is used to increase the spatial resolution and/or contrast of ultrasound imaging, compared to ultrasound imaging assuming a constant sound speed.

For reconstruction of the local echo at position (x,z) the time of arrival $t_1$ of the transmitted ultrasound wave at (x,z) as well as the propagation time delays $t_2(x,z,x')$ of propagation of the echo from (x,z) to the individual probe elements at positions (x',z=0) are conventionally calculated assuming a constant speed of sound, and are used for synthetic focusing of the transducer array to (x,z) as described earlier. A speed of sound different from the assumed speed of sound results in erroneous propagation time delays and thus in defocusing and a suboptimal spatial resolution and contrast of the resulting image. The present invention provides the knowledge of the sound speed that allows accurate calculation of the propagation time delays. Using this corrected delays for image reconstruction, spatial resolution and contrast can be increased compared to assuming a constant sound speed (see e.g. above). Similarly, the distribution of sound speed can be used for optimization of resolution and contrast in optoacoustic (also called photoacoustic) imaging (OA). In OA, ultrasound transients are generated inside the tissue by optical absorption of irradiating pulsed laser light via heating and thermoelastic expansion. The propagation times of an OA transient generated at position (x,z) to the transducer elements at positions (x', z=0) are calculated based on the assumed speed of sound, and used for reconstruction of an image of optical absorption in a way analogous to pulse-echo ultrasound. Knowledge of the spatial distribution of speed of sound allows also here a more accurate reconstruction of optical absorbers, compared to assuming a homogeneous speed of sound.

According to a further embodiment of the present invention, the reconstructed distribution of (e.g. inhomogeneous) sound speed is used to achieve a more accurate geometrical display of ultrasound or optoacoustic images than by assuming a constant sound speed. Conventionally, straight ray ultrasound propagation is assumed when calculating the propagation time delays for synthetic focusing of the array probe in image reconstruction. Acoustic refraction, i.e., the bending of sound beams caused by an inhomogeneous distribution of sound speed results in geometric distortions of the reconstructed image. The present invention particularly provides the knowledge of the inhomogeneous distribution of sound speed that allows accounting for acoustic refraction when calculating the propagation time delays for image reconstruction, resulting in an image with less distortion compared to a conventional image. This is especially advantageous for improved accuracy of ultrasound guided surgical interventions.

According to a further embodiment of the present invention, a spatial distribution of a temperature change inside the object is determined. The local sound speed depends on the local temperature of the tissue. Therefore the evolution of the local temperature relative to an initial reference can be measured two-dimensionally with high temporal resolution using the method according to the invention based on a pre-determined relation between sound speed and temperature. This is promising e.g. for real time feedback in high-intensity-focused-ultrasound cancer surgery.

Further, the problem according to the invention is solved by a computer program having the features of claim 14.

According thereto, the computer program comprises software code, wherein, when executed on a computer, said computer program is designed to reconstruct from backscattered first ultrasound pulse echoes a first image of first local echoes and from backscattered second ultrasound pulse echoes a second image of second local echoes, wherein said backscattered first ultrasound pulse echoes originated from at least a first ultrasound pulse that has been transmitted by means of an ultrasound probe in a first direction ($\varphi_0$) into an object to be imaged, and wherein said backscattered second ultrasound pulse echoes originated from at least a second ultrasound pulse that has been transmitted by means of said ultrasound probe in a different second direction ($\varphi$) into said object, wherein said images lie in an image plane spanned by said directions ($\varphi_0, \varphi$), and to determine from said reconstructed images the respective resulting local echo phase shift $\Delta\tau(x,z,\varphi,\varphi_0)$ at locations (x,z) in said image plane between the respective first local echo and the associated second local echo, and to determine the local sound speed c(x,z) in said object for at least a region of said image plane in said object from said local echo phase shifts $\Delta\tau(x,z,\varphi,\varphi_0)$.

According to a preferred embodiment of the present invention the computer program is further designed to conduct the steps stated in one of the claims 2 to 14 when said computer program is executed on a computer.

Furthermore, the problem according to the invention is solved by a system having the features as described herein.

According thereto said system for determining and particularly imaging sound speed in an object by means of ultrasound, comprises:

an ultrasound probe being designed to transmit at least a first ultrasound pulse in a first direction $\varphi_0$ and a second ultrasound pulse in a different second direction $\varphi$ into an object to be imaged, so that said first ultrasound pulse is backscattered in said object towards said ultrasound probe in the form of first ultrasound pulse echoes, and so that said second ultrasound pulse is backscattered in said object towards said ultrasound probe in the form of second ultrasound pulse echoes, wherein said ultrasound probe is further designed to detect said backscattered first ultrasound pulse echoes and said backscattered second ultrasound pulse echoes, and an analyzing means being designed to reconstruct from said detected backscattered first ultrasound pulse echoes a first image of first local echoes and from said detected backscattered second ultrasound pulse echoes a second image of second local echoes, wherein said images lie in an image plane spanned by said directions $(\varphi_0,\varphi)$ and to determine from said reconstructed images the respective resulting local echo phase shift $\Delta\tau(x,z,\varphi,\varphi_0)$ (being the change in echo time or equivalently the change in z-position) at location (x,z) relative to an assumed constant sound speed in the object) in said image plane between the respective first local echo and the corresponding second local echo (relative to the case of an assumed constant sound speed), wherein said analyzing means is further designed to determine the local sound speed c(x,z) in said object for at least a region of said image plane in said object from the local echo phase shifts $\Delta\tau(x,z,\varphi,\varphi_0)$.

The analyzing means is preferably further designed to conduct the individual steps of the method according to the invention as claimed in one of the claims 2 to 13 (e.g. relating to the calculation of the local sound speed as described above). For displaying sound speed images the system may comprise a display being designed to be connected to the analyzing means. The analyzing means may be formed by a computer on which a suitable software is carried out (e.g. the computer program according to the invention). The ultrasound probe is preferably designed as stated above, i.e., preferably comprises a plurality of ultrasound transducers, particularly arranged in a linear array, so that 2D ultrasound images can be acquired with the probe. Preferably, the probe is a handheld probe.

Further features and advantages of the invention shall be described by means of detailed descriptions of embodiments of the present invention with reference to the Figures, wherein FIG. 1 shows a schematic illustration of the principle of sound speed detection using pulse-echo ultrasound, wherein panels a) and d) show Tx sound paths from the US probe to a scatterer for two different Tx steering angles. According to panels b) and e) the Rx apertures are identical for the two cases. Further, as shown in panels c) and f) the changing speed of sound along the different Tx sound paths leads to a local echo phase shift at the location of the ultrasound scatterer.

Figure 2:
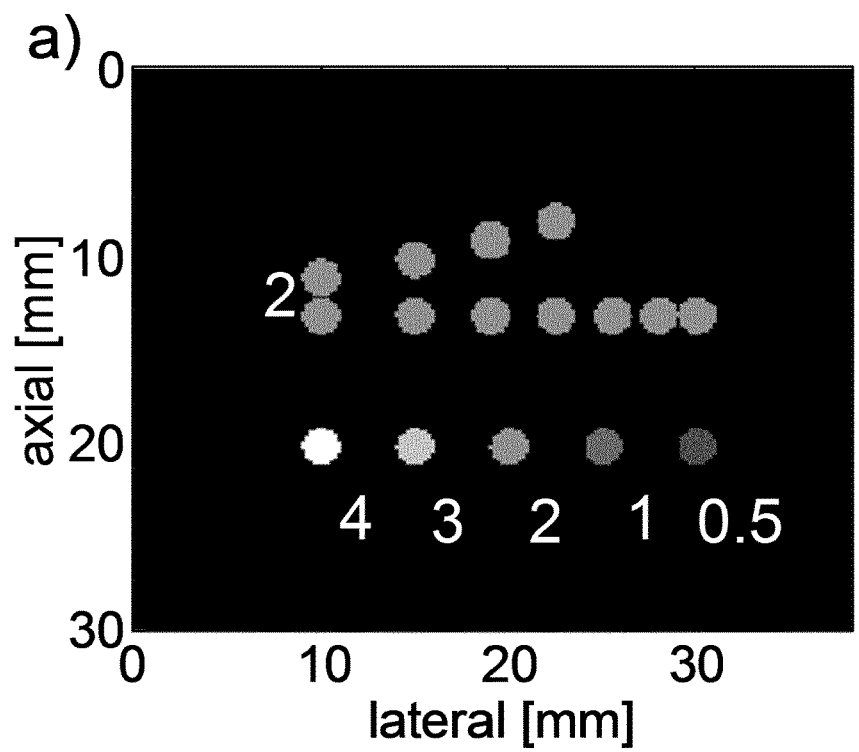
Figure 2:
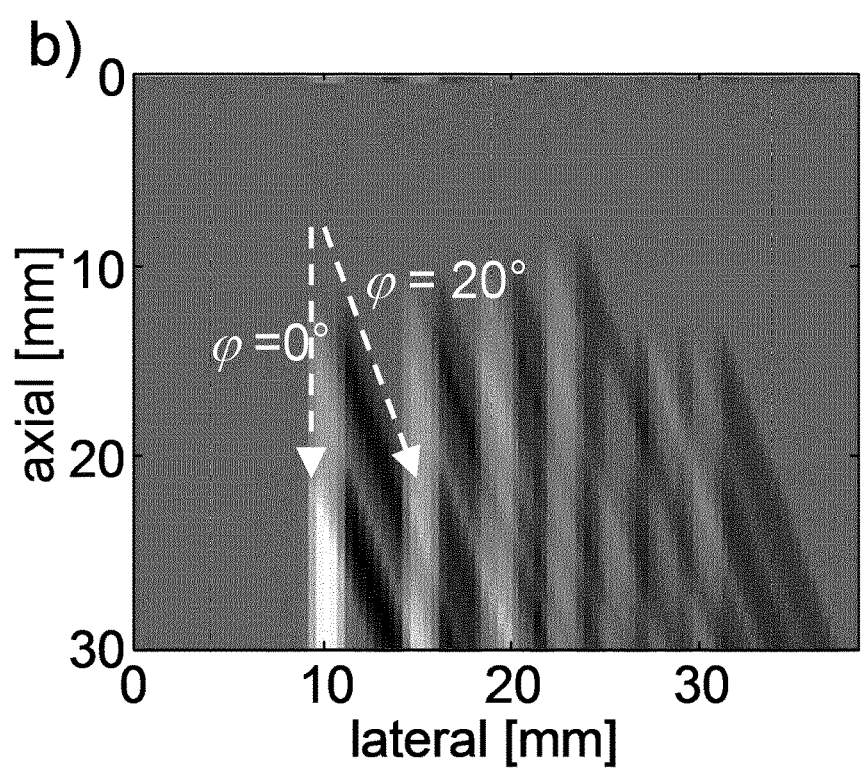

FIG. 2 shows in panel a) a 2D digital phantom with disk-shaped sound speed contrast inclusions, wherein the numbers denote a percentage of sound speed relative to the average sound speed (1540 m/s). Further, panel b) shows the local echo phase shift when changing the Tx angle or direction $\varphi$ from 0° (first direction) to 20° (second direction), assuming straight line sound propagation.

Figure 3:
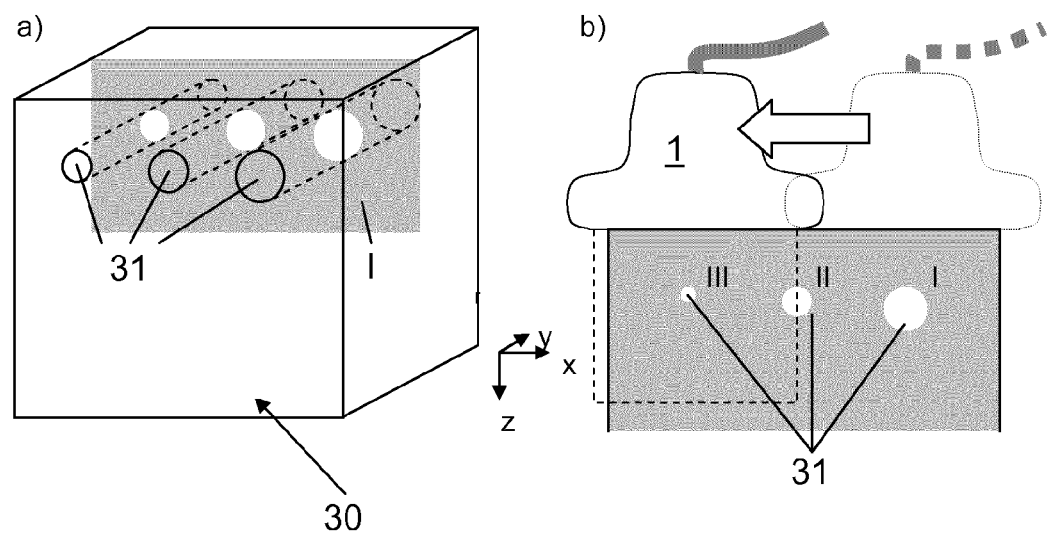

FIG. 3 shows in panel a) a schematic illustration of a phantom, showing the cylindrical inclusions having lower gelatine concentration than the bulk medium, and the location of the scanning plane where pulse-echo data was acquired. The lab coordinate system is also indicated. Panel b) shows a schematical illustration of the setup, showing the ultrasound probe in contact with the top phantom facet. Because the probe aperture was smaller than the phantom facet, the phantom was scanned by the probe with the imaging plane parallel to the scanning plane to acquire pulse-echo data of all inclusions and the surrounding medium.

Figure 4:
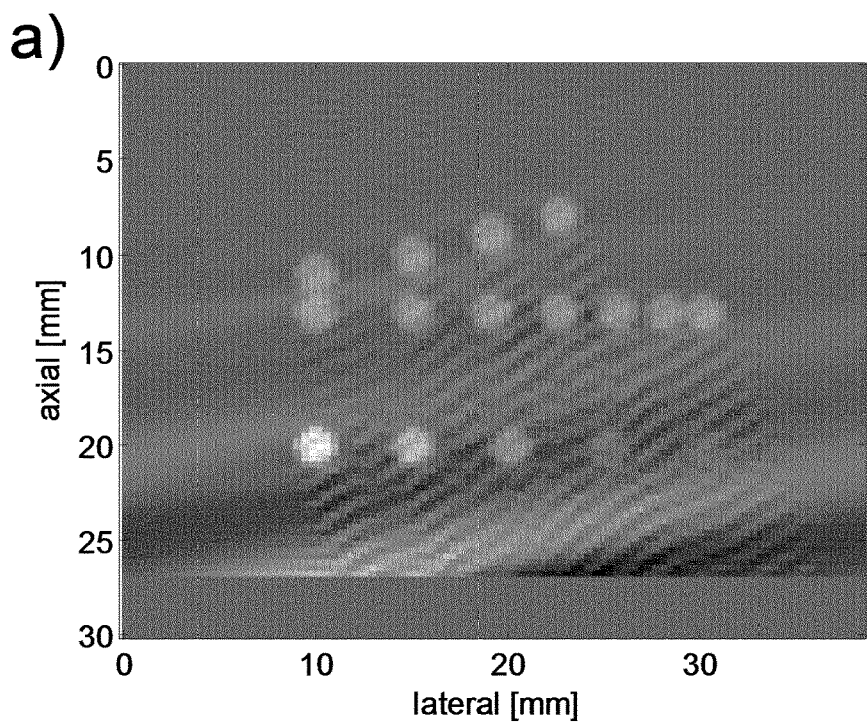
Figure 4:
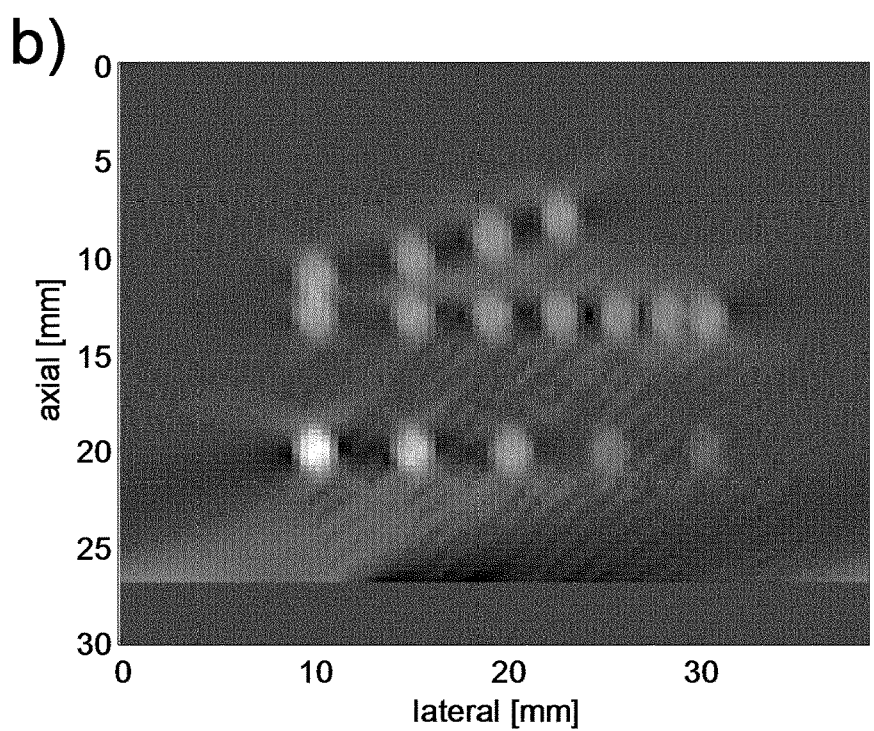
Figure 4:
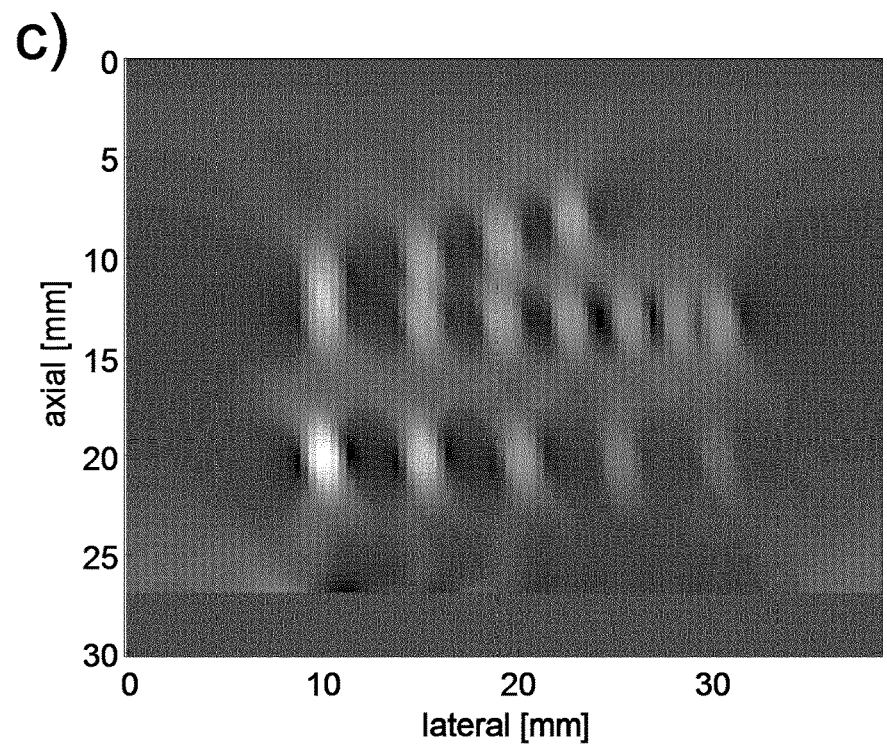
Figure 4:
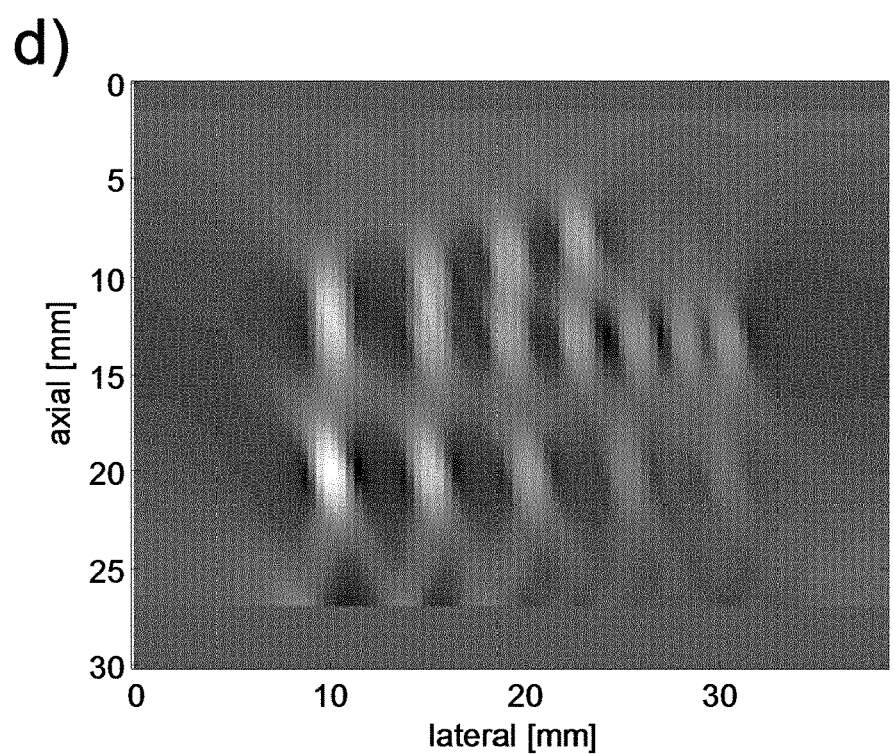
Figure 4:
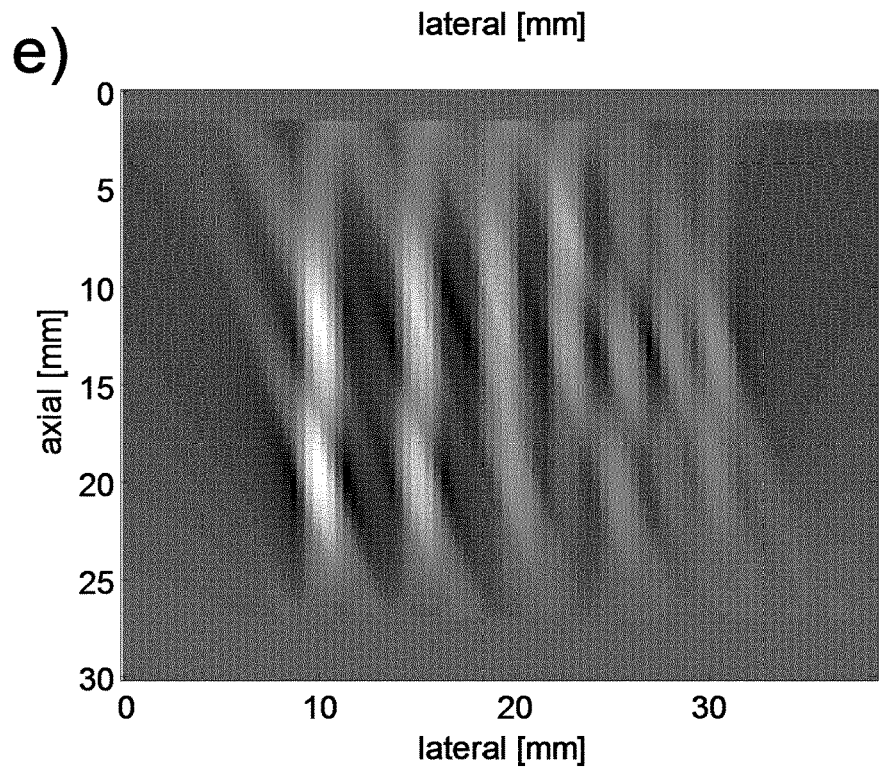
Figure 4:
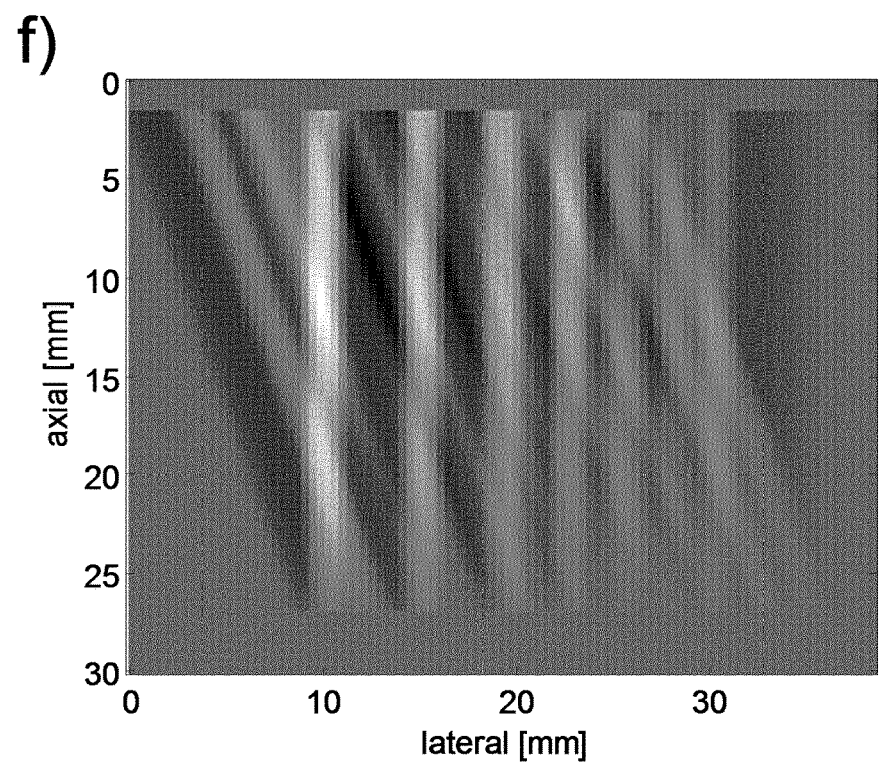

FIG. 4 shows reconstructed sound speed images based on the phase data in FIG. 2b without noise, using different values of the regularisation parameter $\gamma$=20 (panel a)), 100 (panel b)), 500 (panel c)), 1000 (panel d)), 5000 (panel e)), 100000 (panel f)).

Figure 5:
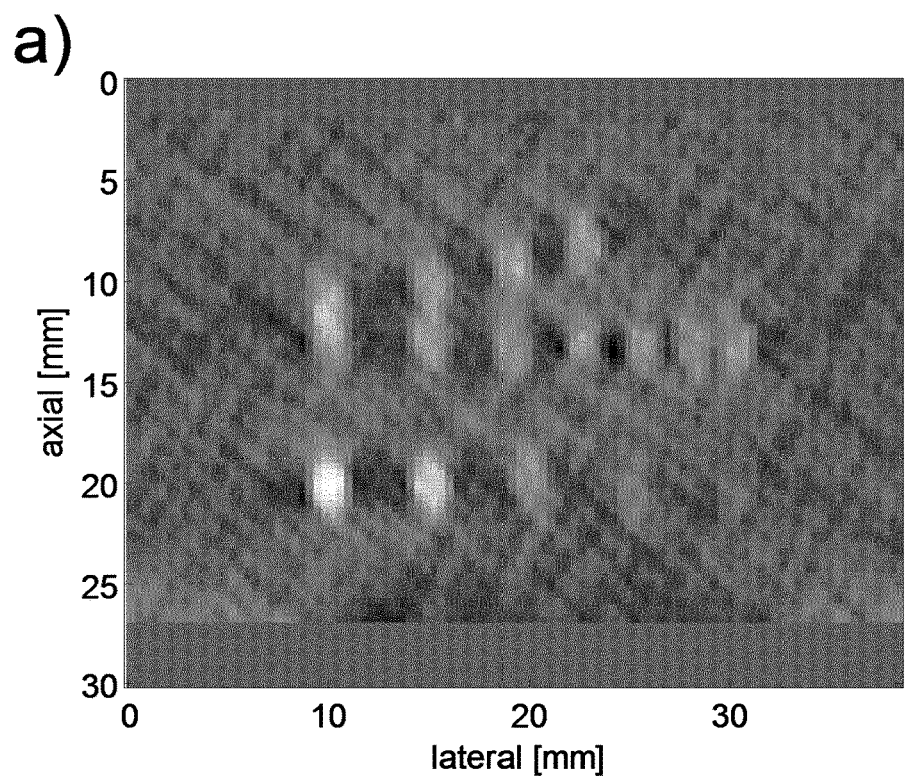
Figure 5:
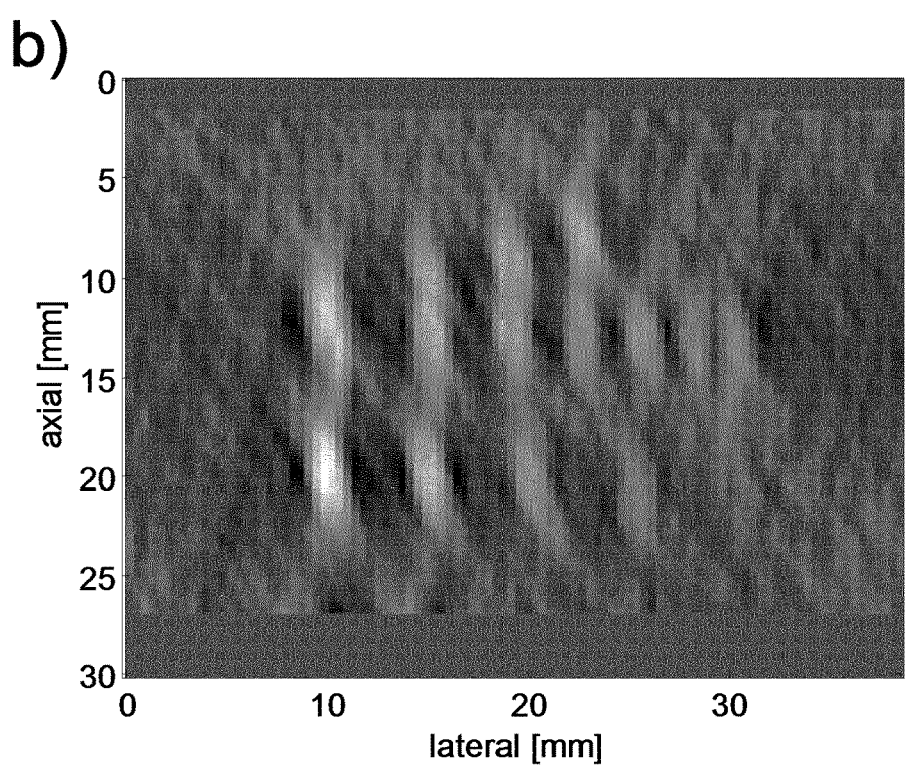
Figure 5:
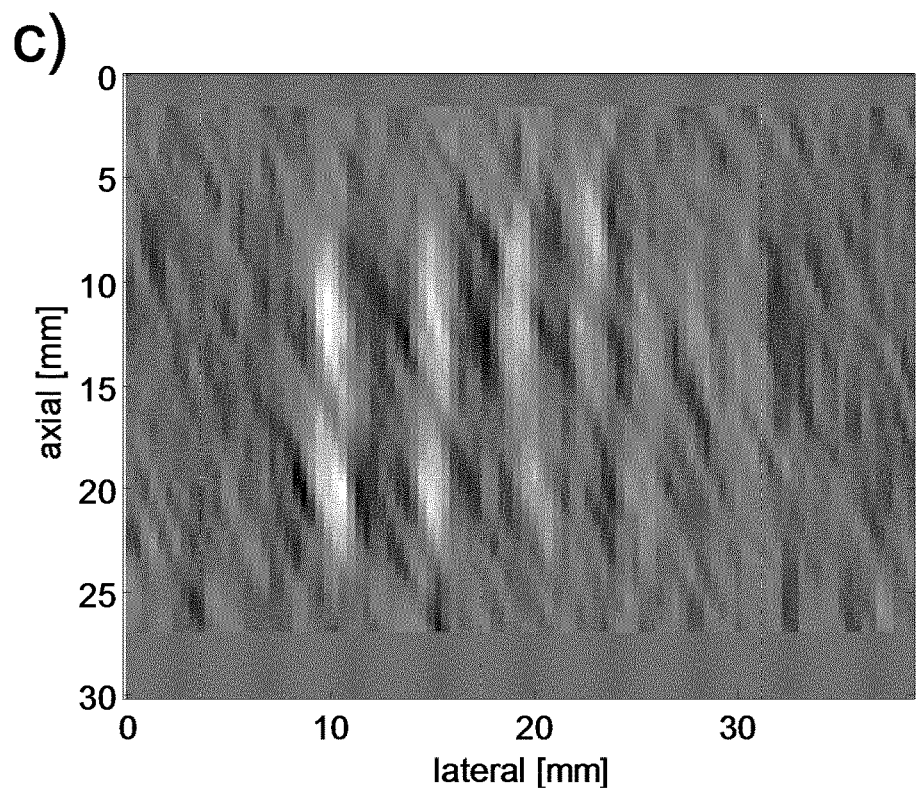
Figure 5:
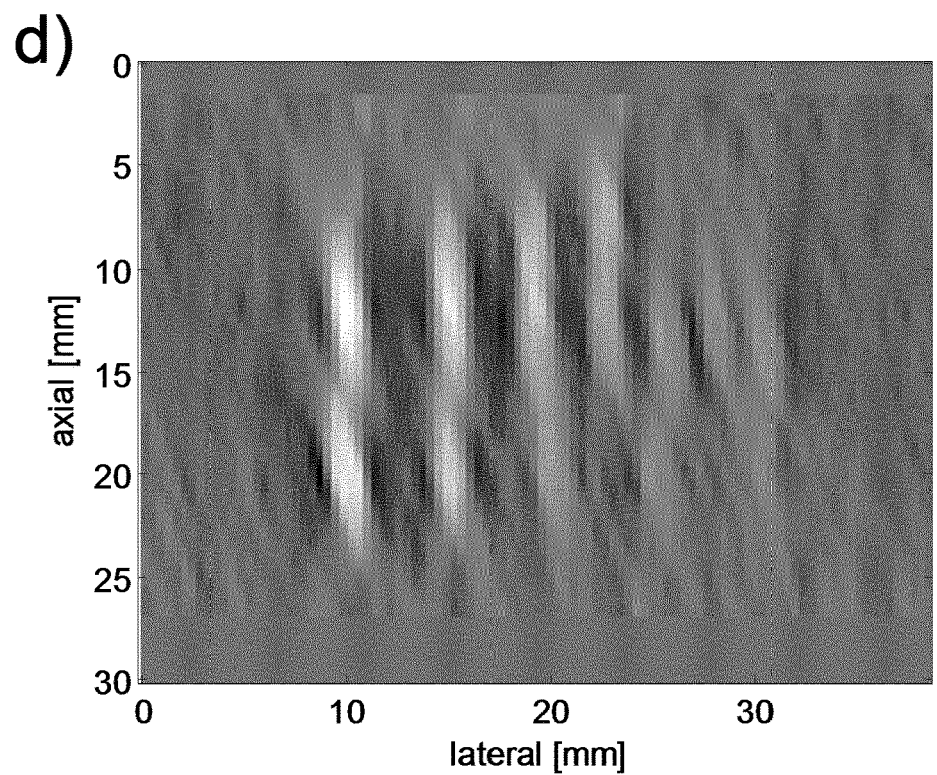

FIG. 5 shows reconstructed sound speed images based on the phase data in FIG. 2b when assuming different noise levels. The regularisation parameter $\gamma$ was separately tuned for each noise level such that the 1% contrast region would become discernible. Panel a) 1% noise relative to maximum phase shift, $\gamma$=300. Panel b) 3% noise, $\gamma$=1300. Panel c) 10% noise, $\gamma$=3000. Panel d) shows the result with 10% noise but using five Tx angles (directions) instead of only two (0°, 5°, 10°, 15°, 20°), $\gamma$=3000. Using more Tx angles has an averaging effect on phase noise and improves contrast.

Figure 6:
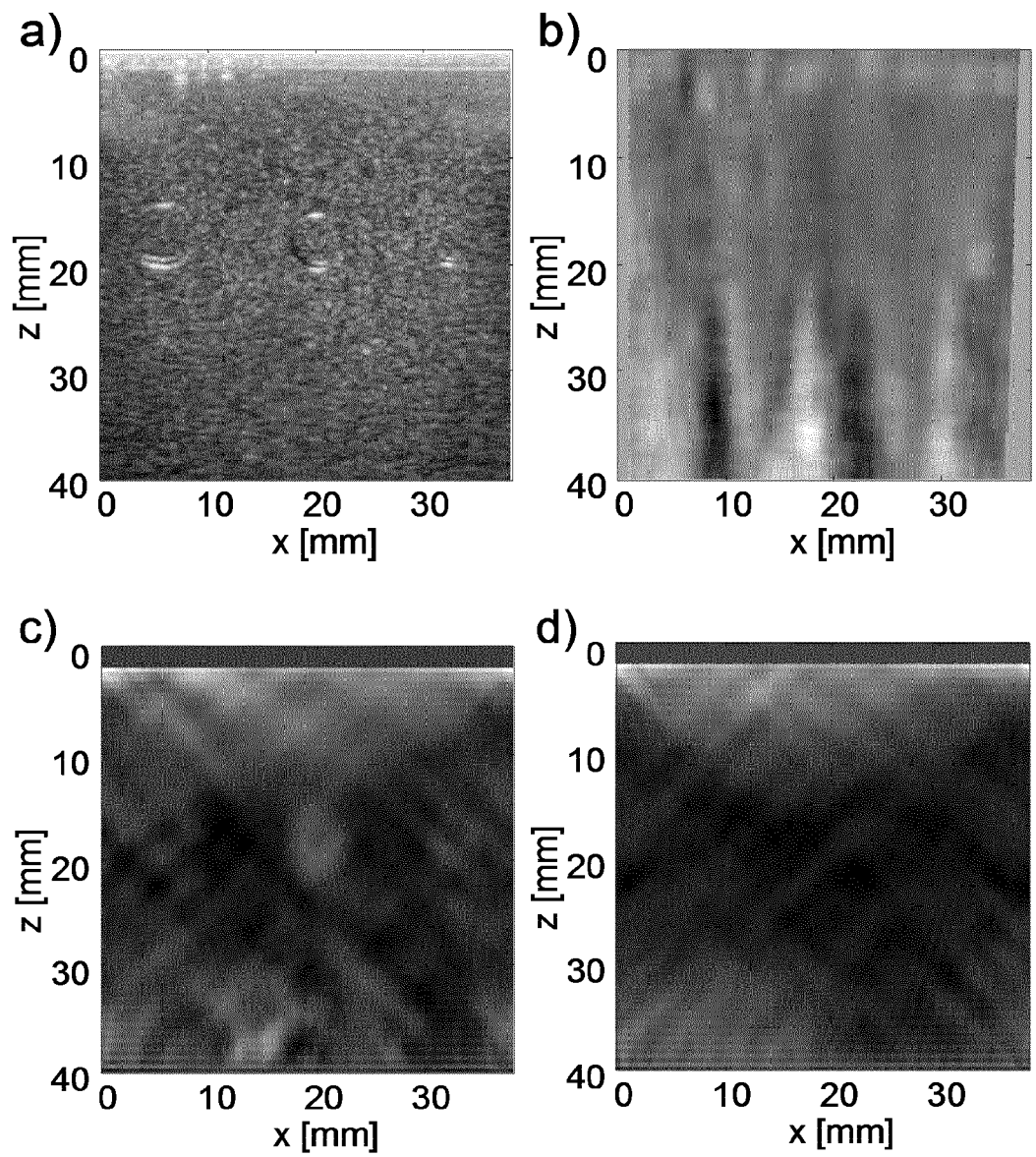

FIG. 6 Panel a) shows a B-mode image of the phantom where inclusion II was located. The B-mode image shows no contrast for the inclusion apart from specular reflections. Panel b) shows the map of the local echo phase shift when changing the Tx angle by 2°. This data was accumulated for successive Tx angles, ranging from −30° to 30°. Panel c) shows the sound speed (CUTE) image reconstructed from accumulated echo phase shift data from Tx angles −30°, −20°, −10°, 10°, 20°, 30° with reference angle 0°. This reveals the presence of a region with lower sound speed. An inverted greyscale was chosen for better visibility. Panel d) shows for comparison a CUTE image from a control phantom region where no inclusion was located.

Figure 7:
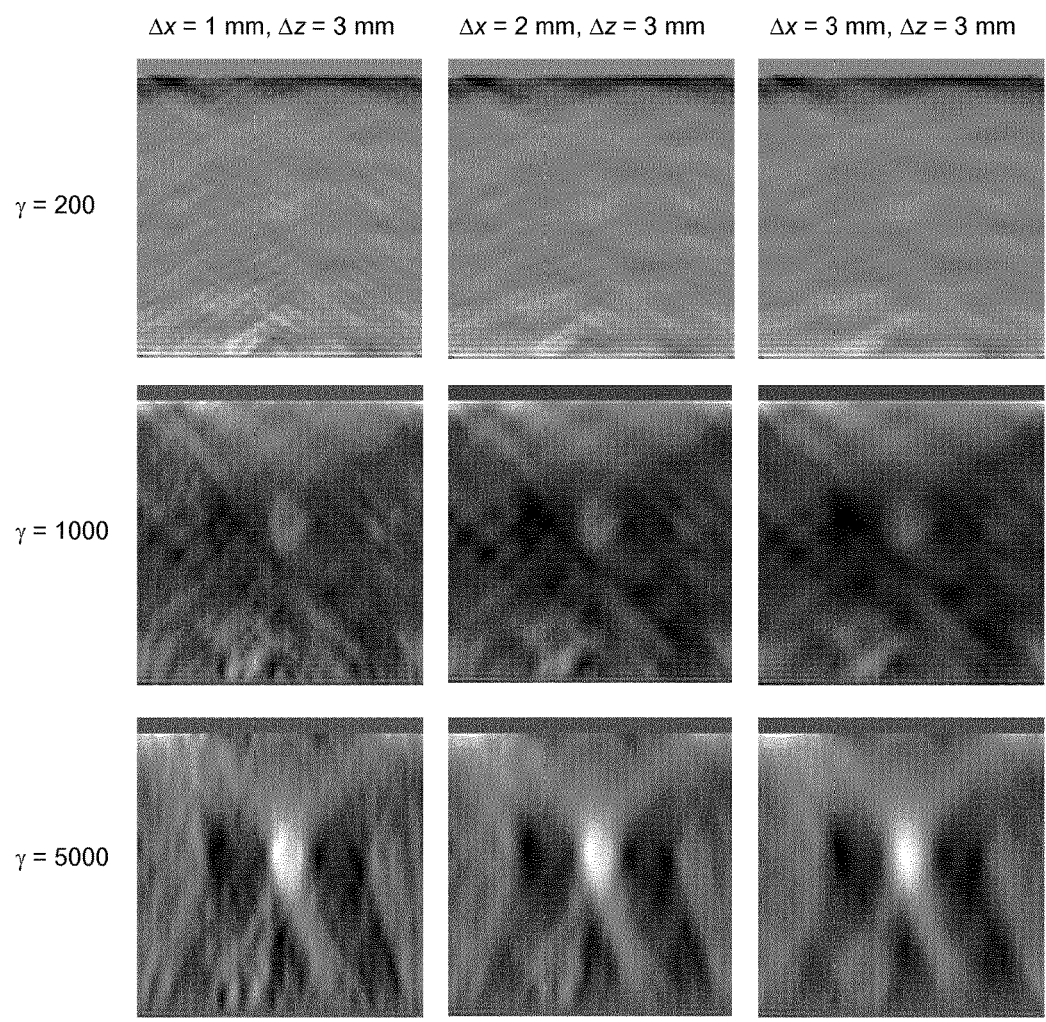

FIG. 7 shows sound speed (CUTE) images of inclusion II illustrating the different contrast that is obtained with different choices of the tracking kernel ($\Delta x$, $\Delta z$) and of the regularisation parameter $\gamma$.

Figure 8:
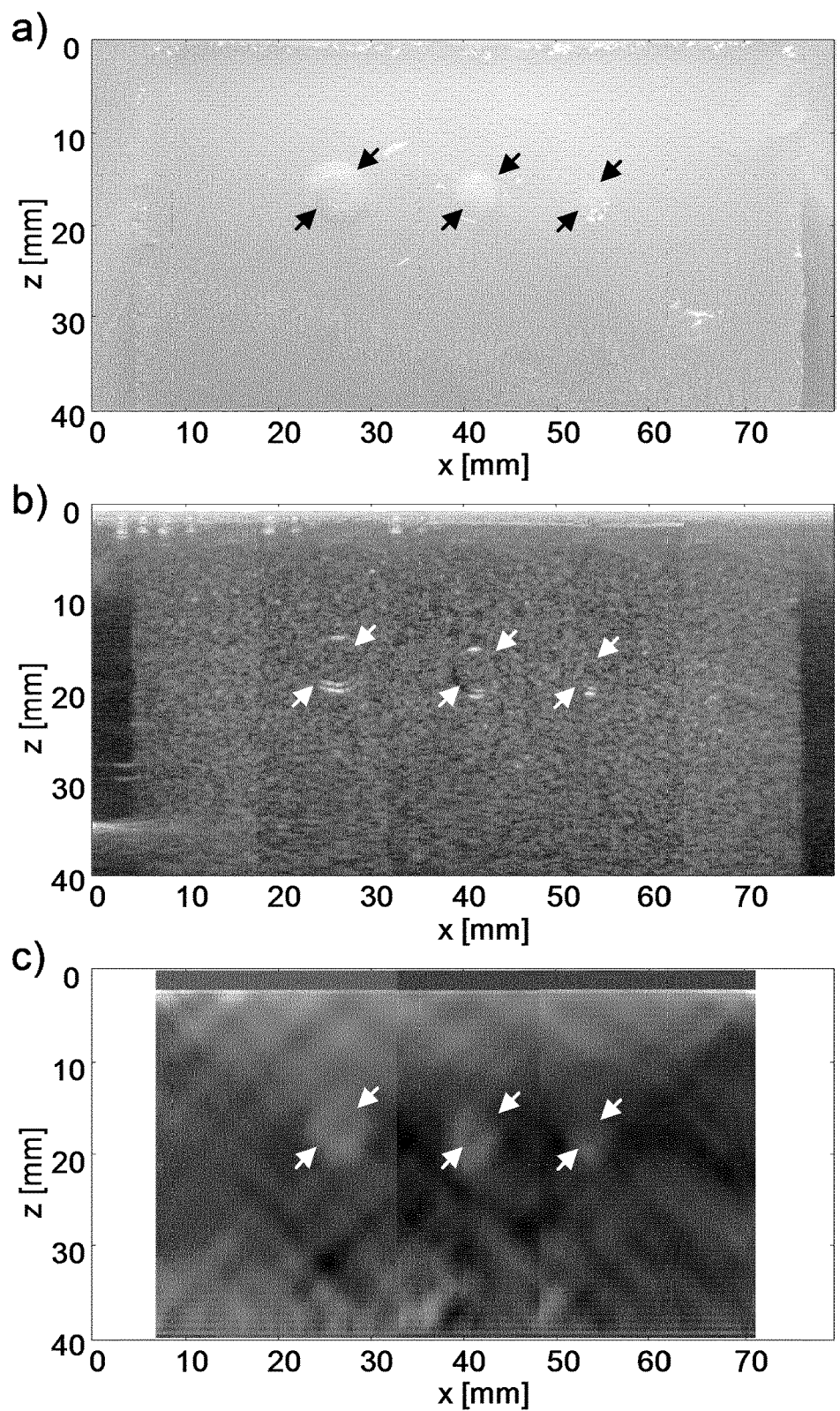

FIG. 8 shows a demonstration of the correlation of sound speed contrast with inclusion location. Panel a) shows a picture of a section through the phantom along the plane where pulse-echo data was acquired, with inclusion locations denoted by arrows. Panel b) shows a B-mode ultrasound panorama which was generated by registering B-mode images that were obtained when scanning the phantom parallel to the imaging plane. Panel c) shows a sound speed (CUTE) image panorama which was generated from the different sound speed (CUTE) images, using the registration that was found for (b). The outermost left and right images are not shown because they exhibited too strong artifacts caused by the absence of ultrasound scatterers outside the phantom. The arrows demonstrate the correct registration between the sound speed contrast and the inclusion locations.

Figure 9:
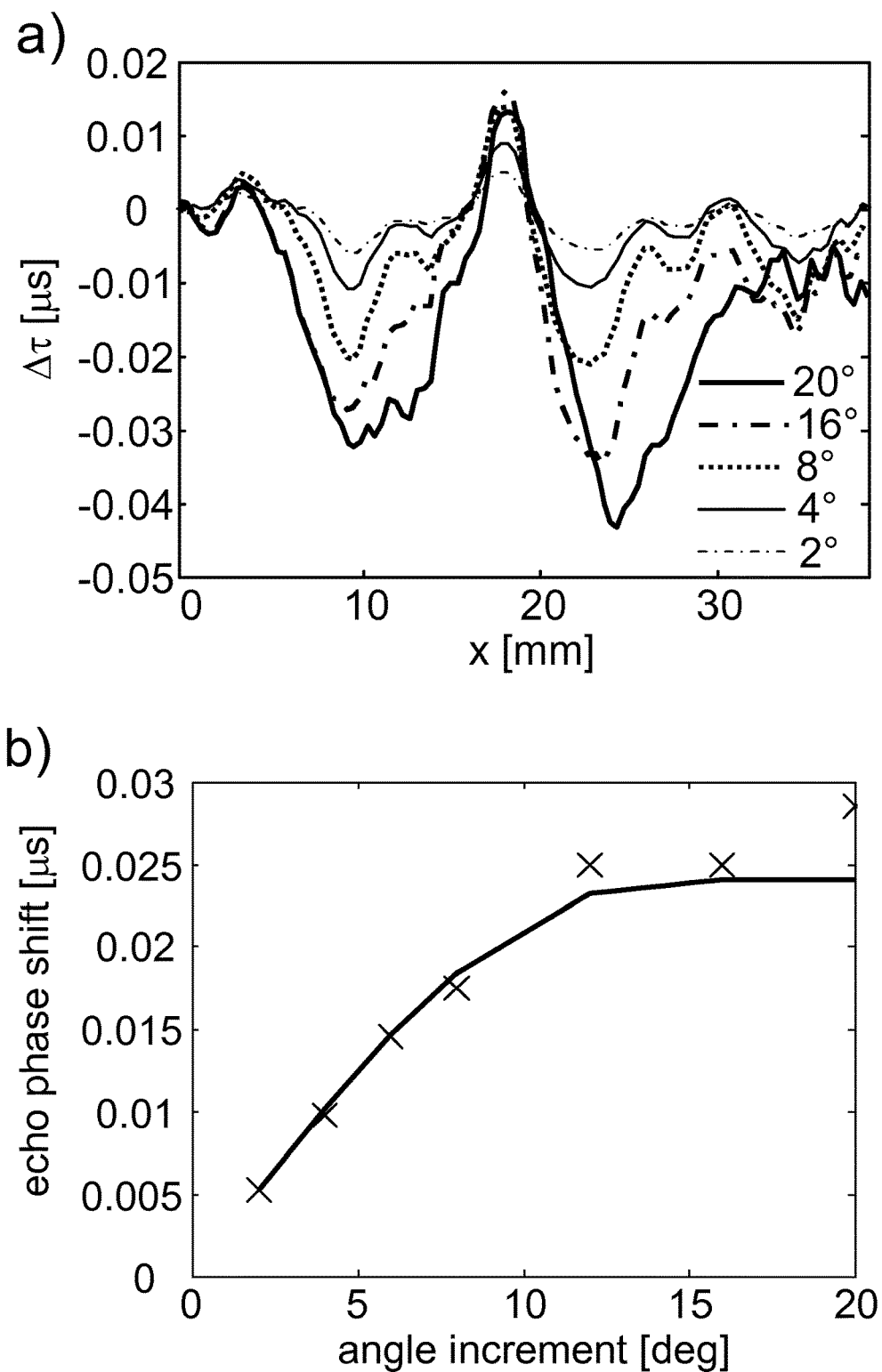

FIG. 9 Panel a) shows profiles of the echo phase shift at the lower edge of the image for different Tx angle increments. Panel b) shows a plot showing the maximum phase shift as a function of the angle increment. The experimental data (crosses) is fitted using the model of Eq. (8) (solid line).

Figure 10:
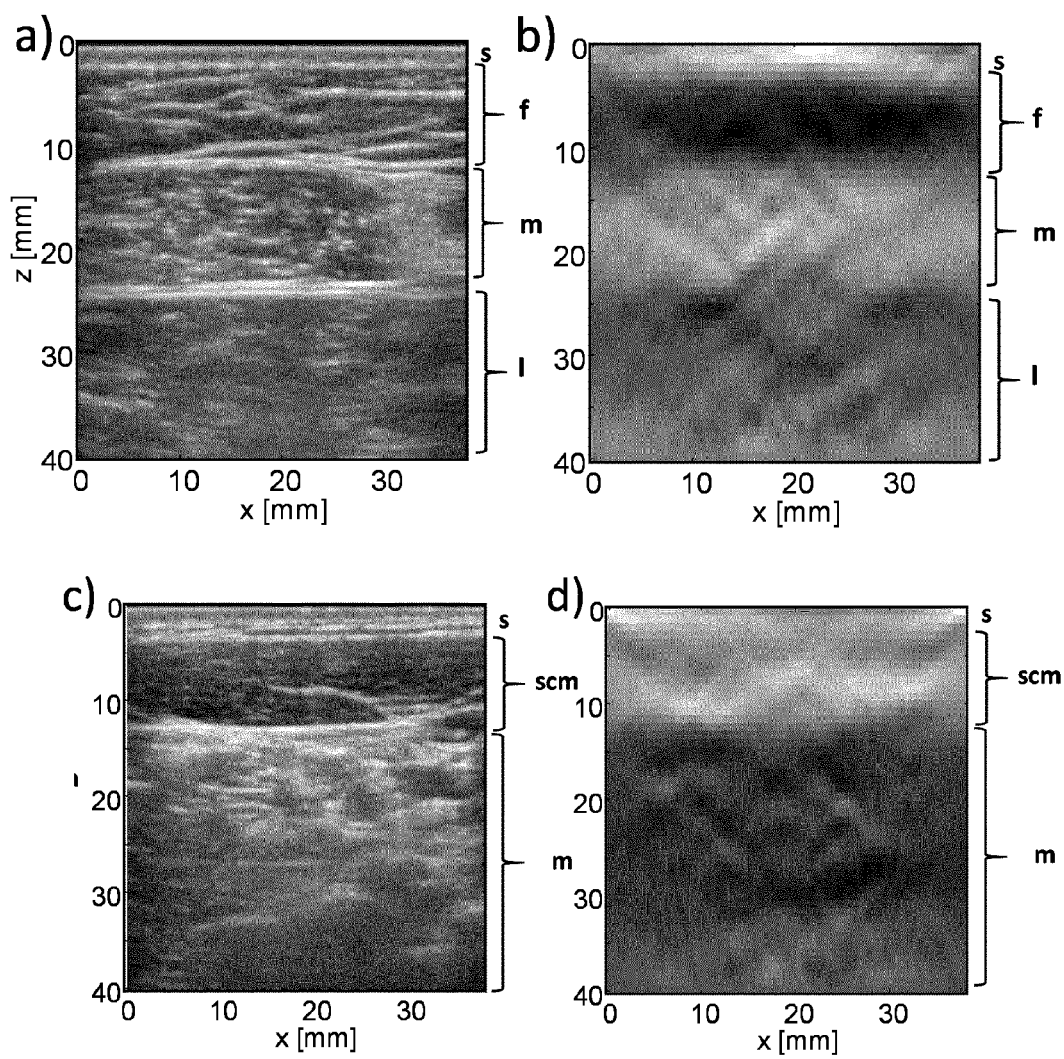

FIG. 10: Panel a) shows the B-mode US (60 dB) of the abdominal wall, with the skin (s), subcutaneous adipose tissue (f), musculature (m), and liver (l). Panel b) shows the corresponding CUTE image. Panel c) is the B-mode US (60 dB) of the neck, with the skin (s), sternocleidomastoid (scm), and deeper muscles (m). Panel d) shows the corresponding CUTE image.

Figure 11:
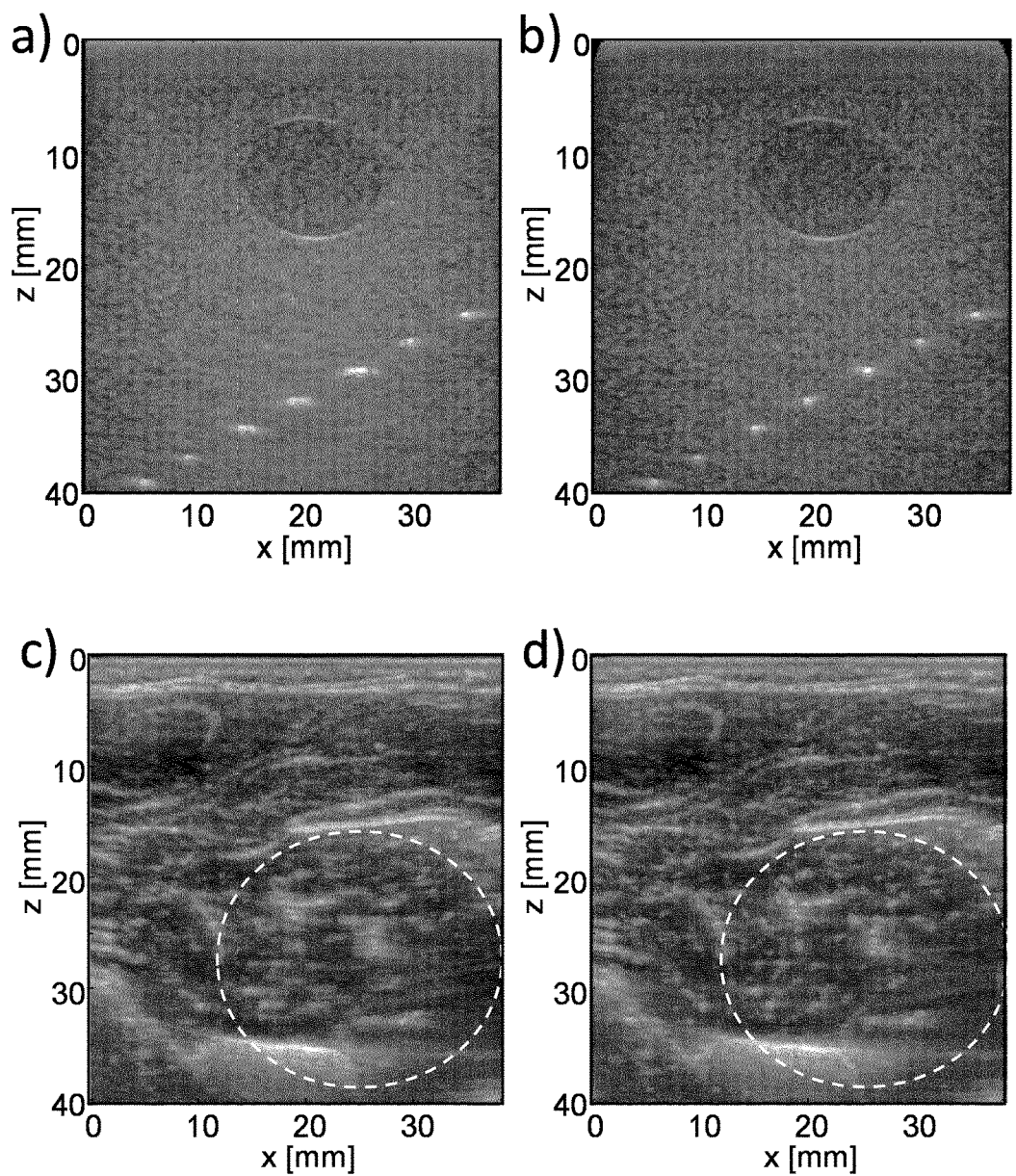

FIG. 11: demonstrates aberration correction based on CUTE. Panel a) is the B-mode US image of a phantom that was reconstructed assuming a homogeneous speed-of-sound. Panel b) is the corresponding B-mode US image after aberration correction. Panel c) is the B-mode US image of a volunteer forearm assuming a homogeneous speed-of-sound. Panel d) is the corresponding image after aberration correction.

FIG. 1 shows the underlying principle of the present invention. For simplicity, we assume that a linear array probe 1 transmits a first ultrasound pulse 10 in the form of a plane ultrasound transient in a first direction, i.e., at a transmit (Tx) angle $\varphi_0$, by choice of the transmit timing of the individual array elements or transducers 1a of the probe 1 (only one element 1a is indicated in FIG. 1 as an example). The plane transient 10 propagates through the object's O tissue that contains a spatially confined sound speed contrast region 2 (region with e.g. higher sound speed). Below the contrast region 2, part of the wave 10 is backscattered by a hypothetical point scatterer 3 in the form of a first backscattered pulse echo 11, here a spherical sound wave, and is detected using the full probe aperture, irrespective of the Tx angle (FIG. 1b)). The receive beam-forming generates the sum of the ultrasound signals detected at all the individual array elements of the probe 1, compensating for the individual time delays of arrival and thus virtually focusing the probe 1 to the acoustic scatterer 3. This results in the radio-frequency (RF) A-line 4, where a wavelet 5 (first local echo) occurs at time $t=t_1+t_2$ after ultrasound transmission (FIG. 1c)). Here, $t_1$ is the transit time of the transient from the probe 1 to the scatterer 3, and $t_2$ is the transit time of the scattered spherical transient 11 back from the scatterer 3 to the probe 1. The $t_1$ is adjusted for the effect of the difference of propagation path lengths (from the transducer to the scatterer) owing to the different Tx angle.

In FIG. 1a), the transmit (Tx) wave arrives at the hypothetical scatterer after having propagated along the path indicated by a wedge which is not influenced by the contrast region 2. This situation however changes when the Tx angle changes from $\varphi_0$ to $\varphi=-\varphi_0$ (FIG. 1d)). Now, the part of the Tx wave, denoted as second ultrasound pulse 20, which arrives at the scatterer 3 has transited the contrast region 2. Therefore it arrives earlier at the scatterer 3 than in the hypothetical case where sound speed contrast is zero, leading to a shorter $t_1$ (cf. FIG. 1f) where the second local echo, i.e., wavelet 7, has a shorter echo time in A-line 6 compared to wavelet 5). A positive contrast leads to a decrease of $t_1$, a negative contrast to an increase of $t_1$, respectively. At the same time, nothing changes for the second backscattered ultrasound pulse echo 21 (e.g. spherical wave), i.e., $t_2$ is not influenced by the Tx angle (FIG. 1e)). The echo time t can thus be expressed as $t=t_0+\tau(\varphi)$, where $\tau$ is the additional local echo phase caused by the sound speed contrast, relative to the hypothetical case of zero contrast (constant sound speed reference everywhere). This phase reflects the deviation of the sound speed from the reference value, accumulated along the acoustic line of propagation from the probe to the acoustic scatterer. When scanning the Tx angle $\varphi$, tracking the echo phase therefore provides a means of probing sound speed along lines of different direction.

In analogy to UCT, the wavelet 5 in FIG. 1c) can be regarded as the signal which is recorded by a virtual point sensor (located at the position of the point scatterer 3), of the Tx pulse 10 after having propagated through the tissue in-between the probe 1 and the scatterer 3. When changing the Tx angle $\varphi$, only the transmit part of the ultrasound propagation path from the probe 1 to the scatterer 3 changes, whereas the receive part remains the same. The role of the receive path can be regarded as a wireless data connection that uses ultrasound as a carrier field, via which the data is transferred from the point sensor (scatterer 3) to the antenna (probe 1) connected to the data processing unit (US system). In this view, a collection of point scatterers 3 acts like a collection of ultrasound receivers, which transmit their respective data via different wireless channels back to the same antenna 1.

In principle one could choose a collection of such "receivers" arranged along a line below the contrast region 2, and perform a transmission-tomographic reconstruction of the contrast region 2 like in UCT based on the Tx angle dependent echo phase in these locations. This approach would, however, result in a very poor image of the sound speed: The range of possible Tx angles is limited both by the limited angular aperture of the single transducer elements 1a and by the limited aperture of the full transducer array 1. In UCT (as well as in CT) the missing of the line integral values along directions outside such a limited angle range results in image degradations such as directional blurring and streak artifacts ("limited view artifacts").

In the method according to the invention (CUTE), however, the effect of the limited angle range is (partially) outweighed by the much larger availability of data. Because biological tissue is naturally characterised by densely distributed ultrasound scatterers 3 (apart from hypoechoic regions such as blood vessels), hypothetical point sensors 3 of echo phase are available also inside the region where sound speed shall be reconstructed. The present invention demonstrates that this availability of local echo phase data inside a contrast region allows for the reconstruction of a spatially resolved sound speed map from as little as only two Tx angles (directions).

For the reconstruction of the sound speed based on the local echo phase, a very simple model of sound propagation is adopted: The arrival time t of the Tx pulse at the scatterer at a position (x,z) in the imaging plane is entirely determined by the line integral of the slowness (inverse of sound speed) along a straight line between the probe aperture and the scatterer, with an angle $\varphi$ relative to the axial direction z. I.e. no sound refraction or diffraction is taken into account. For any $\varphi$, the local echo phase $\tau(x,z,\varphi)$, i.e., the change in arrival time compared to a medium with homogeneous reference slowness $\sigma_0$ everywhere, is:

$$\sigma(x, z) \doteq \frac{1}{c(x, z)} - \sigma_0, \tag{1}$$

$$\tau(x, z, \varphi) = \sqrt{1 + \tan^2\varphi} \cdot \int_0^z dz' \sigma(x - z\tan\varphi + z'\tan\varphi, z')$$

In practise, $\tau$ cannot be determined in an absolute way because the true position z of scatterers is unknown. Only the relative echo phase shift between different Tx angles can be measured. For didactic reasons, however, we assume in a first step that the echo phase can be measured in an absolute way, for each $\varphi$ separately and everywhere in the imaging plane. The transformation from a (x,z) to $\tau(x,z,\varphi)$ can be represented by a linear operator $M(\varphi):\tau=M(\varphi)\sigma$, where $\sigma$ and $\tau$ are vectors that contain all the slowness values and the measurement values, respectively, and σ could then be reconstructed by the inversion of M(φ). For this purpose, M(φ) is conveniently expressed in the discrete spatial frequency domain, as a matrix with elements $M_{k',k}$ that describe the transformation of the discrete Fourier transform (DFT) σ(k) of G to the DFT τ(k') of T. For deriving this matrix, σ is in a first step thought of as a superposition of harmonic components $σ_k$ with wave vectors k:

$$σ_k(x, z) \doteq \exp[ik_x x + ik_z z] \Rightarrow \quad (2)$$

$$τ(x, z, φ)_k = \sqrt{1 + \tan^2 φ} \cdot \int_0^z dz' σ_k(x - z\tan φ + z'\tan φ, z')$$

$$= \sqrt{1 + \tan^2 φ} \cdot \int_0^z dz' \exp[ik_x(x - z\tan φ + z'\tan φ) + ik_z z']$$

$$= \sqrt{1 + \tan^2 φ} \cdot \exp[ik_x(x - z\tan φ)] \cdot \frac{1}{i(k_x \tan φ + k_z)}$$

$$\{\exp[i(k_x \tan φ + k_z)z'] - 1\}$$

In a second step, the DFT of $τ_k$ over the image region with dimensions X (laterally) and Z (axially) results in $M_{k',k}$:

$$M_{k',k}(φ) \doteq \iint_{X,Z} dx\,dz\,τ(x, z, φ)_k \exp[-ik'_x x - ik'_z z] \quad (3)$$

$$= \ldots$$

$$= \frac{\sqrt{1 + \tan^2 φ}}{i(k_x \tan φ + k_z)} \cdot X \cdot δ(k_x - k'_x) \cdot \ldots$$

$$\left\{ Z \cdot δ(k_z - k'_z) + \frac{1}{i(k_x \tan φ + k'_z)} \{\exp[-i(k_x \tan φ + k'_z)Z] - 1\} \right\}$$

δ is the Kronecker-delta function. Eq. 3 states that all elements $M_{k',k}$ where $k_x \neq k_x'$ are zero, thus inversion of M can be efficiently performed for each $k_x$ separately.

Now we take into account that in practise, τ can only be measured relative to a reference angle $φ_0$. The operator $T(φ,φ_0)$ that transforms σ to the relative echo phase shift $Δτ(φ,φ_0)$ is:

$$Δτ(φ,φ_0) = T(φ,φ_0) \cdot σ$$

$$T(φ,φ_0) = M(φ) - M(φ_0) \quad (4)$$

Unfortunately, inversion of T turns out to be an ill-conditioned inverse problem: A full inversion of T does not lead to a suitable reconstruction of σ because small errors in τ are heavily amplified. For a regularised reconstruction of σ one therefore employs the Tikhonov pseudo-inverse instead $$T^{-1} \doteq (T^*T + Γ^*Γ)^{-1} T^*, \quad (5)$$

which minimises the expression $$\|τ - Tσ\|^2 + \|Γσ\| \quad (6)$$

where * denotes the complex transpose, and Γ is the regularising term. For the following results Γ was chosen to be the identity matrix, multiplied with a real-valued regularisation parameter γ. This corresponds to regularisation by minimisation of the mean-squared σ, in agreement with the assumption that σ shall be close to zero. After inverse DFT of the reconstructed σ to space-domain, the sound speed is obtained according to the first line in Eq. 1.

EXAMPLE 1

In a first example it was demonstrated that the method according to the present invention (CUTE) is feasible in principle, using the above described concept and reconstruction algorithm. The goals of this step were along following lines:
  demonstration of the feasibility of tomographic reconstruction of sound speed with high spatial resolution, using only two Tx angles (one reference angle plus one additional angle) and evaluation of the influence of the regularising parameter γ on the reconstructed image. The phase τ(x,z,φ) is assumed to be accurately known (no noise).
  demonstration of tomographic reconstruction when noise is taken into account. In practise, the local phase shift when changing the Tx angle is determined using tracking of the local echo phase in the reconstructed images (e.g. A-lines). Noise can originate from thermal noise, but most significantly from tracking errors due to speckle decorrelation with changing Tx angle.

For the purpose of this example, synthetic data of the local relative echo phase shift with changing Tx angle was generated for a 2D digital phantom of the sound speed distribution in the imaging plane of a linear probe. This phantom contained disk-shaped lesions with 2 mm diameter and 0.5% to 4% higher sound speed than the background tissue. This is a reasonable range of contrast because soft tissue sound speed ranges within 5% of the average value of 1540 ms$^{-1}$, and sound speed in breast cancer is 3% to 5% larger than in the surrounding glandular tissue and subcutaneous fat [10].

FIG. 2a) shows the digital phantom as well as the local relative echo phase shift when changing the Tx angle from φ=0° to φ=20° (FIG. 2b)). Numbers in FIG. 2a) denote the percentage of sound speed relative to the average sound speed (1540 m/s). The echo phase for different angles was numerically calculated in the space-domain according to Eq. 1 assuming straight ray sound propagation. The physical dimension of the image aperture was chosen in agreement with the dimensions of the linear probe that was used for the experiment described below (example 2), i.e. 37 mm.

The generation of synthetic data as well as the reconstruction method described above were implemented in Matlab-code.

EXAMPLE 2

For an experimental proof-of-principle, a Verasonics ultrasound system (Verasonics Inc., WA, USA) was employed. This dedicated research system allows ultrasound transmission on 128 channels (two-board version) and signal acquisition on 64 channels simultaneously, as well as the fast data transfer to a host computer via a PCI Express link. We implemented a dedicated script for the acquisition of CUTE data from a HDI L7-4 broadband linear vascular probe (ATL Philips, WA, USA). This probe features 128 elements at 0.29 mm pitch, and a bandwidth from 4 to 7 MHz with 5 MHz centre frequency. The script steered the acquisition of plane-wave pulse-echo data using Tx angles ranging from −30° to 30° in steps of 0.5°.

As shown in FIG. 3a) a phantom 30 was built from porcine gelatine (Geistlich Pharma, Switzerland) with cellulose (Sigmacell Type 20, Sigma-Aldrich, Germany) for ultrasound scattering. A solution with 15% gelatine (by mass) in water was prepared, dissolved at 60° C., and 0.2% (by mass) cellulose added ("mixture 1"). Part of this solution was separated and further diluted in water to yield a 7.5% gelatine and 0.1% cellulose mixture ("mixture 2"). Mixture 1 was cooled down close to the gelation point of 34° C., gently stirred to evenly distribute the cellulose, and then cast into a pre-cooled cubic mould and cooled down in the fridge to obtain the phantom bulk with dimensions 7 cm (x-axis) by 7 cm (z-axis) by 4 cm (y-axis). Three cylindrical holes with different diameters were then cut into the bulk, parallel to one of the 7 by 4 cm facets. These holes were then filled with gelatine mixture 2 to provide cylindrical inclusions 31 with different sound speed than the phantom bulk. After completion, the phantom was placed inside a water tank. The probe 1 was covered with a condom to make it water tight, taking care that no air bubbles were trapped in-between the probe aperture and the latex skin. The probe 1 was then placed onto the phantom facet on the side where the inclusions 31 were located, with the imaging plane I aligned perpendicular to the cylindrical inclusions 31. FIG. 3b) shows a schematical view of the setup with the ultrasound probe 1 being in contact with the top phantom facet. Because the probe aperture was smaller than the phantom facet, the phantom 30 was scanned by the probe 1 with the imaging plane I parallel to the scanning plane to acquire pulse-echo data of all inclusions 31 and the surrounding medium.

For each Tx angle, a separate pulse-echo RF frame was reconstructed on the host computer using a frequency-domain reconstruction algorithm. Such a plane-wave pulse-echo frame contains a high level of clutter. The reason for this is that the receive beam alone is focused in plane-wave imaging whereas the unfocused Tx wave transmits significant acoustic power into the medium surrounding the receive beam which then couples into the receive beam via multiple acoustic scattering. Such clutter significantly added to phase noise, making the local RF phase difficult to use in the present method. In comparison, conventional US usually uses an e.g. narrow transmit beam confocally with the receive beam such that the acoustic power transmitted into the medium outside the receive beam is minimal. Also line-by-line scanning can be employed within the framework of the present invention, it may have several disadvantages when being used for CUTE, including a large number of acquisitions required for a single image, susceptibility to motion artifacts, and phase errors along the borders between adjacent transmit beams. Therefore, in order to obtain pulse-echo frames with lower clutter, preferably a synthetic aperture (SA) approach is applied, where confocal pulse-echo frames are synthesised from plane-wave frames. For this purpose, for each target Tx angle $\varphi$, a group of plane-wave frames that were obtained with Tx angles ranging within $[\varphi-\Delta\varphi,\varphi+\Delta\varphi]$ were coherently averaged (i.e. the reconstructed RF A-lines were averaged, prior to envelope detection). $\Delta\varphi$ was chosen such as to yield a synthetic Tx beam angular aperture of 5°. An angle step of 0.5° was sufficiently fine to adequately reproduce the angular spectrum of the synthetic Tx beam. This procedure resulted in an image with significantly reduced clutter equivalent to a line-by-line image, and allowed robust local phase tracking. In addition, the total number of acquisition events per image was only 11, compared to several tens of lines that are used for line-by-line scanning.

For tracking the local echo phase we employed a baseband correlation (see e.g. [4]). The point-wise hermitian product of the complex amplitudes (after Hilbert transform of the RF-lines) of successive frames is calculated, and then low-pass filtered by convolution with a tracking kernel of size $\Delta x$ (laterally) and $\Delta z$ (axially). The local phase shift is then estimated as the argument of the resulting complex map. This method can be used as long as the local phase shift is smaller than $\pi$, a condition that is easily satisfied with small Tx angle steps.

With $-30°$ as a starting angle, the echo phase shift in-between successive SA frames was gradually accumulated for all Tx angles up to $+30°$, resulting in phase maps $\sigma(x,z,\varphi,\varphi_0=-30°)$. After storage of this data, the phase maps could be recalculated for any desired reference angle. For sound speed reconstruction an angle set of $\varphi=[-30°, -20°, -10°, 10°, 20°, 30°]$ was finally chosen, with reference $\varphi_0=0°$.

In a first step, tomographic reconstruction of sound speed using the method according to the invention is investigated in a numerical study. FIGS. 4 and 5 show the results, based on the numerical phantom and data from FIG. 2.

In FIG. 4, reconstructed sound speed images based on the phase data in FIG. 1b without noise are shown using different values of the regularisation parameter $\gamma=20$ (panel a)), 100 (panel b)), 500 (panel c)), 1000 (panel d)), 5000 (panel e)), 100000 (panel f)). FIG. 4a) demonstrates the feasibility of the method according to the invention (CUTE) with full spatial resolution using only two Tx angles. This result stands in contrast to UCT where ultrasound transmission from a large number of angles is required for a tomographic reconstruction. In UCT, using only two angles would result in severe streak artifacts and a very low spatial resolution. The reason why only two angles are sufficient in the present method is the availability of phase data everywhere in the image as opposed to the availability only outside the sample in UCT. To achieve this result, a very small $\gamma$ had to be chosen where the ill-posedness of the reconstruction results in low frequency artefacts that disturb the baseline of the bulk sound speed, as well as in high frequency artefacts that spread downwards through the image. Choosing a slightly higher $\gamma$ reduces such artefacts and a nicer image is obtained with still good spatial resolution (FIG. 4b)). However, one can now discern slight artefacts, i.e. blurring of the upper and lower edges of the contrast regions and a drop of the base line adjacent to the left and right edges. Similar artefacts are well known as "limited view artefacts" both in CT and UCT when the view angle range is smaller than the full range of 180°. With growing $\gamma$ (FIGS. 4c) and d)) artefacts due to the ill-posedness of the reconstruction are further reduced, but the "limited view artefacts" become stronger, resulting in gradual loss of axial resolution. For very large $\gamma$ (FIGS. 4e) and f)) the outcome finally converges to an image which pretty much looks like a CT image that was acquired using only two angles, with severe streak artefacts and strongly reduced axial resolution.

FIG. 5 shows reconstructed sound speed images based on the phase data in FIG. 2b when assuming different noise levels. The root-mean-square noise level was set at 1% (FIG. 5a)), 3% (FIG. 5b)), and 10% (FIG. 5c)) of the maximum phase shift. Due to the ill-posedness of the sound speed reconstruction, a low regularisation parameter $\gamma$ results in noise amplification. Because the regularisation parameter $\gamma$ also influences spatial resolution, noise leads to a trade-off between resolution and contrast. For each noise level, the regularisation parameter $\gamma$ was chosen such that the 1% sound-speed contrast region would just be visible. This resulted in stronger regularisation and thus lower spatial resolution for increasing noise level. Above 10% noise level, no value could be found for $\gamma$ that would have lead to visibility of the 1% contrast region. The reason for this is that above $\gamma=3000$, streak artefacts from the different contrast regions become significant and superpose to "ghost"

contrast regions (remember FIGS. 4e) and f)). Up to now, sound speed was reconstructed based on the echo phase shift between only two Tx angles, i.e. 0° and 20°. FIG. 5d) shows the result when reconstructing from a larger set of Tx angles simultaneously. This has an averaging effect on phase noise in the sound speed image, as can be seen by comparing to FIG. 5c).

EXAMPLE 3

Further an experimental test of the present method according to the invention was conducted using phantom data acquired with a real US system. In practise, the local phase shift may be determined using echo phase tracking, which is prone to errors. A main error source is the speckle decorrelation that occurs due to the changing point-spread function when changing the Tx angle [2, 3], which sets a lower limit to phase noise and thus to contrast and resolution.

FIG. 6 shows results of the method according to the invention (CUTE) when imaging the phantom 30 at the location of inclusion 31 (II). The location of this inclusion 31 is visible on conventional B-mode US (FIG. 6a)) due to the specular reflections at the sharp acoustic impedance mismatch of the inclusion boundary. Apart from specular reflections, the inclusion shows no contrast of speckle intensity, similar to e.g. a cancer with unsuspicious echogenicity that blends in with the surrounding tissue. The reason for this lack of contrast is the similar concentration of ultrasound scatterers in comparison to the bulk medium. Even though the average scatterer concentration differs by a factor of two, such contrast is insignificant in comparison to the strong intensity variation of US speckle. The influence of the different sound speed on echo phase, however, is significant. This can be seen in the local echo phase shift when changing the Tx angle by only 2° around the 0° angle (FIG. 6b)). Consequently, the sound speed (CUTE) image reconstructed from such echo phase data reveals the presence and location of the inclusion 31 with significant contrast and resolution (FIG. 6c)). Note that the sound speed contrast is shown in inverted gray scale, i.e. the image indicates that the inclusion 31 had a lower sound speed than the bulk medium. For comparison, a CUTE image was generated from a different phantom region where no inclusion was located (FIG. 6d)), revealing a much more homogeneous background. Both FIG. 6c) and FIG. 6d) show similar artefacts close to the upper and lower edges of the image, which indicates that such artefacts are independent of the presence of the inclusion 31 and can be compensated for.

As illustrated by the numerical results in FIG. 5, the regularisation parameter $\gamma$ determines the image quality along a trade-off between contrast and resolution in presence of echo phase noise. In practise, a second trade-off between phase noise and resolution exists, determined by the phase tracking kernel size. A large kernel size results in robust phase tracking but low spatial resolution, and vice versa. In order to determine optimum parameters, FIG. 7 shows results of the method according to the invention (CUTE) for various different choices for the regularisation parameter $\gamma$ and the tracking kernel size ($\Delta x, \Delta z$). This illustrates the influence of the different parameters on the image contrast and resolution, and finally we decided for $\gamma=1000$, $\Delta x=2$ mm and $\Delta z=3$ mm. The images in FIGS. 6c) and 6d), as well as the images in FIG. 8, were obtained using these values.

After having demonstrated the ability of the method according to the invention to reveal contrast in presence of an inclusion 31 with different sound speed than the surrounding bulk medium, it must be proven that this contrast is spatially linked to the inclusion location. For this final step, a reference was required that would show the inclusion location independent of the present method (CUTE). In our experiment, B-mode ultrasound revealed the position of the inclusions 31 I and II and thus could serve as such a reference, but inclusion 31 III was only partially visible on B-mode so a further reference was needed. For this reason, the correct location of the inclusions 31 was additionally determined by photography. FIG. 8a) shows a photograph of a section through the phantom 30, obtained after the experiments at the location of the imaging plane. In this section, the inclusions were visible due to slight differences in optical refractive index and due to difference in stiffness which lead to slight concave deformation of the section surface after cutting. The locations and approximate size of the inclusions 31 is indicated. FIG. 8b) shows a panorama of B-mode US images that were acquired while scanning the phantom surface with the imaging probe 1 parallel to the imaging plane I. The various B-mode images were registered based on common contrast details. FIG. 8c) shows the corresponding panorama of sound speed images generated with the method according to the invention that were acquired together with B-mode US. Finally, the B-mode panorama was registered with the phantom photograph, yielding the location of the inclusions 31 in relation to the B-mode and the CUTE panoramas. FIG. 8c) demonstrates the correct registration between CUTE contrast and the inclusion locations, supporting the assumption that CUTE contrast was indeed caused by the inclusions 31.

Both the numerical and the experimental results consistently demonstrate that the method according to the present invention (CUTE) facilitates imaging of the sound speed based on the pulse-echo signal. This allows sound speed imaging in reflection mode using hand-held probes, and thus the imaging of body parts that are not accessible to UCT opening a wider field of application.

The numerical results demonstrate that, in principle, CUTE allows the accurate reconstruction of the spatially resolved sound speed with high spatial resolution using only two Tx angles, as opposed to UCT where a large range of Tx angles is required for a tomographic image. The reason for this is that CUTE reconstruction of sound speed can make use of local information of the echo phase inside a contrast region, which is not available in UCT. However, this local information can only be fully taken advantage of in the absence of noise when the regularisation can be low. With growing strength of regularisation, the resulting CUTE image gradually converges to an image with no axial resolution and with artefacts. The reason is that the local echo phase reflects not only local sound speed, but also average sound speed along a "line" of ultrasound propagation from the transmitting probe to the local ultrasound scatterers. When changing the Tx angle, most of the echo phase change is due to the changing accumulative effect of sound speed along different lines of propagation. With strong regularisation, only the accumulative information is used for reconstruction. Then the reconstruction of a contrast region is fully dependent on the echo phase below this region similar to UCT, and the resulting image suffers from the same limited-view artefacts that result from a limited Tx angle range. The local information carries axial resolution but is more susceptible to noise, whereas the accumulated information has virtually no axial resolution but is robust against noise. The regularisation parameter $\gamma$ determines to which grade accumulated information is favoured over local information, and somewhere in-between the two extremes, a medium choice of γ results in an image with both good contrast and axial resolution.

The experimental results confirm the feasibility of CUTE when using real phantom data, and illustrate that CUTE has the potential to diagnose lesions that are unsuspicious on conventional B-mode US. As such, CUTE is promising as an additional diagnostic modality that can complement conventional US alongside with other novel methods such as elastography and photoacoustic imaging. As a diagnostic modality, CUTE has the potential to distinguish between tissue lesions that may have similar echogenicity on B-mode US but different speed of sound, such as cancer and cysts, or fatty and fibrotic regions in fatty liver disease and liver fibrosis. For diagnostic purposes, the contrast resolution (minimum resolvable contrast at a given spatial resolution) is of interest. The sound speed contrast in the phantom experiment could in principle be determined from the reconstructed image. However, because of regularisation, part of the spatial frequencies of the image are missing and the pixel grey level does not directly represent sound speed. For now, we maintain that the sound speed can also be determined based on the local echo phase shift (FIG. 6b) directly if the shape of the inclusion is assumed to be known. A disk-shaped inclusion cross-section with diameter D and sound speed contrast E leads to a time delay $T_{max}$ of the part of the Tx wave that propagates through the middle of the inclusion, relative to the part that propagates through the background medium with sound speed $c_0$:

$$\tau_{max} = \frac{D}{c_0 \cdot (1+\varepsilon)} - \frac{D}{c_0} \cong -\frac{D}{c_0}\varepsilon \Rightarrow \varepsilon \cong -\tau\frac{c_0}{D} \quad (7)$$

The inclusion leads to a delay profile $\tau(x,\varphi)$ at a depth z behind the inclusion, which has maximum amplitude $T_{max}$ in the middle of the "shadow" of the inclusion, and drops to zero outside. The relative echo phase shift $\Delta\tau(x,\Delta\varphi)$ when changing the Tx angle by $\Delta\varphi$ is the difference of two shifted versions of this profile, $\tau(x,\varphi+\Delta\varphi)-\tau(x,\varphi)$. We approximate the profile $\tau(x,\varphi)$ with a cosine, and derive an expression for the resulting amplitude $\tau_{max}$ of the profile of the relative echo phase shift:

$$\tau(x, \varphi) = \tau_{max} \cdot \frac{1}{2}\left\{\cos\left[\pi\frac{x-x_0-(z-z_0)\varphi}{W}\right]+1\right\} \quad (8)$$

$$\Delta\tau(x, \Delta\varphi) \equiv \tau(x, \varphi+\Delta\varphi) - \tau(x, \varphi) \Rightarrow$$

$$\Delta\tau_{max} = \tau_{max} \cdot \frac{1}{2}\left|\cos\left[\pi\frac{W-(z-z_0)\Delta\varphi}{2W}\right] - \cos\left[\pi\frac{W+(z-z_0)\Delta\varphi}{2W}\right]\right|$$

(where $x_0$ and $z_0$ are the position of the centre of the inclusion, and W is the width of the "shadow")

FIG. 9a shows the experimental profile of $\Delta\tau$ obtained close to the lower edge of the echo phase shift map in FIG. 6b, ($\Delta\varphi=2°$) together with profiles for other Tx angle increments. FIG. 9b shows a plot of the $\Delta\tau_{max}$ obtained from those profiles, as function of $\Delta\varphi$. This data was fitted using the result from Eq. (8), to determine the "shadow" width W and the total phase delay $\tau_{max}$ caused by the inclusion. The results were W=5 mm and $\tau_{max}$=0.024 µs. Assuming an inclusion diameter of D=5 mm (derived from the photograph) and using Eq. (7), the sound speed contrast was thus approximately 0.8%. Thus a region with 0.8% sound speed contrast and 5 mm diameter could be detected with 1 mm lateral resolution and excellent contrast. This experimental results is promising that the present method (CUTE) has sufficient contrast and spatial resolution for successful diagnostic imaging.

EXAMPLE 4

In preparation for clinical pilot studies, the system that was described under Example 3 was tested in volunteers. FIG. 10 shows examples that demonstrate the capability of CUTE to distinguish the different speed-of-sound in different tissue layers in the abdomen and in the neck. The B-mode image of the abdomen (a) shows the skin, the subcutaneous adipose, muscles, and finally the liver. The corresponding CUTE image (b) shows the expected high SOS of the skin and the muscle, the low SOS of the adipose, and the intermediate SOS of the liver tissue. The B-mode US in (c) is taken on the neck and shows a superficial muscle layer, plus more muscle layers below. The CUTE image (d) shows a high SOS for the superficial layer but a lower SOS for the deeper muscles. This result was reproducible and consistent for other sites such as forearm and leg, and suggests a different SOS for fast- than for slow-twitching muscles.

Unlike UCT, the method according to the invention does not require ultrasound transmission through the tissue and works well with a limited angle range because it can use local in addition to accumulated information, making it over-all suitable for use with clinically established handheld ultrasound. With Robinson's and Krücker's method the present method shares the concept of misregistration when scanning the tissue from different directions. However, the present method measures the registration error using the echo phase which is much more sensitive to sound speed variations than using the envelope, and in addition a direct sound speed reconstruction method is provided that allows for generating sound speed images with high spatial resolution. With the beam-tracking method CUTE shares the concept of sound speed measurement based on echo times along different sound propagation paths. However, here, the echo phase shift is used which is much more sensitive to sound speed variations as opposed to the centroid of the envelope of the pulse-echo signal, for which reason it yields better spatial resolution. Another method which in principle allows imaging of sound speed in reflection mode is reflection tomography. However, reflection tomography can only reconstruct spatial frequencies of local sound speed variation that can be sampled by the frequency response of the imaging system. With the limited frequency response of medical ultrasound systems, reflection tomography can only recover variations on scales in the order of an acoustic wavelength at the probe's centre frequency. This typically results in an image not much different from a conventional B-mode ultrasound image without significant additional information. In comparison, CUTE allows the reconstruction of sound speed variations on much larger spatial scales, and in combination with reflection tomography, it could help recovering the missing spatial frequency data.

EXAMPLE 5

In addition to complementing conventional US as a diagnostic modality, knowledge of spatially resolved sound speed is promising for aberration correction and thus improved resolution and more accurate geometrical display of conventional B-mode US. This can substantially benefit US in its traditional use in diagnosis as well as in USassisted interventions. Whereas optimisation of spatial resolution by the choice of assumed average sound speed can help to improve image quality in adaptive imaging, short-scale spatial variations of sound speed can often result in significant residual aberration. In adaptive beam forming, a phase screen in front of the probe aperture is often assumed as a model for the accumulative effect of sound speed inhomogeneities. In the presence of strong point scatterers that generate a coherent signal over a large part of the probe aperture, this phase screen is directly reflected in the element-to-element phase variation of the signal. These phase variations can then be compensated for, resulting in an image which shows improved resolution in the region surrounding the point scatterer. However, ideal point scatterers are seldom in real tissue, and the signal at the probe aperture is rather a superposition of incoherent random echoes and extended specular reflections, making aberration correction difficult. In the present method according to the invention, the changing echo phase with changing Tx angle is evaluated in the beam-formed A-lines as opposed to the transducer element signal data. In this way, ambiguities that are linked to speckle and specular reflections and normally occur in the element signal data are avoided. By tracking the Tx angle-dependent echo phase instead of the Rx angle-dependent phase the present method proves to be very robust against such error sources. The present method according to the invention yields a direct reconstruction of a spatial map of sound speed as opposed to a one-dimensional phase screen, and thus it is promising as a novel method for fast, robust, and accurate aberration correction.

FIG. 11 demonstrates aberration correction based on CUTE. FIG. 11a is the B-mode US image of a phantom that was reconstructed assuming a homogeneous speed-of-sound. The circular region with 10 mm diameter at 10 mm depth had a speed-of-sound contrast of 2% relative to the background. As a consequence of the resulting aberration of the ultrasound wavefronts, the bright echoes below the inclusion as well as the background speckle pattern are significantly blurred. CUTE allows quantification of the aberrations and thus an accurate reconstruction of a B-mode US image where the aberrations are compensated for. The resulting image (FIG. 11b) shows both the bright echoes as well as the background speckle pattern with strongly improved spatial resolution. Similarly, aberration correction based on CUTE improves spatial resolution of clinical B-mode US. FIG. 11c is the conventional B-mode US image of a volunteers forearm assuming a homogeneous speed of sound. Inside the region denoted by a dashed circle, significant lateral blurring is observed. FIG. 11d is the corresponding B-mode US after aberration correction based on CUTE. Uniform spatial resolution is obtained independent of the lateral position of echoes.

It is to be noted, that often in real tissue, strongly hypoechoic regions such as large blood vessels lead to regions of missing data in the local echo phase shift maps. Such regions of missing local data will have to be accommodated for in image reconstruction if artefacts are to be avoided. For blood vessels, a simple way of doing this could be an interpolation of the phase shift data assuming a homogeneous sound speed inside the vessel. A more general way of accommodating for missing local data could be to split the reconstruction into two parts, one based on accumulated data, and one based on local data only. A compound image of both parts could then be generated which shows sound speed based on accumulated data only inside regions of missing data, but sound speed based on local data outside. Further, the reconstruction algorithm is based on straight ray ultrasound propagation, neglecting ultrasound diffraction and refraction. In case this assumption cannot be justified in a certain situation observed ultrasound refraction and diffraction may be compensated for by iterative techniques that are already well established in UCT. Because the present method is to a large part based on local information as opposed to accumulated one, it seems likely that diffraction and refraction have less influence on the present method than on UCT, and that therefore less iterations will be needed to achieve a good result.

Summarizing, the present method according to the invention demonstrates that imaging of sound speed inside tissue with high spatial resolution is feasible in reflection mode using conventional hand-held pulse-echo ultrasound. Further, this method is real-time capable and has the advantage of a much more flexible and thus a broader clinical application range of sound speed imaging as opposed to transmission mode computed tomography. In phantom experiments it was shown that the method according to the invention can reveal an inclusion with 0.8% sound speed contrast with 1 mm resolution, a performance index that suggests that this method can be successfully employed for diagnostic imaging.

REFERENCES

[1] N. Duric, P. Littrup, O. Rama and E. Holsapple, "Computerized ultrasound risk evaluation (CURE): First clinical results", Acoust Imag 28(3), 173-181 (2007)
[2] M. Kondo, K. Takamizawa, M. Hirama, K. Okazaki, K. Iinuma and Y. Takehara, "An evaluation of an in vivo local sound speed estimation technique by the crossed beam method", Ult Med Biol 16(1), 65-72 (1990)
[3] P. N. T. Wells, "Ultrasonic imaging of the human body", Rep. Prog. Phys. 62(671-722 (1999)
[4] M. O'Donnell, A. R. Skovoroda, B. M. Shapo and S. Y. Emelianov, "Internal Displacement and Strain Imaging Using Ultrasonic Speckle Tracking", IEEE Trans Ult Ferr Freq Cont 41(3), 314-325 (1994).

The invention claimed is:
1. Method for determining sound speed in an object by means of ultrasound, comprising the steps of:
transmitting by means of an ultrasound probe (1) at least a first ultrasound pulse (10) in a first direction ($\varphi_0$) and a second ultrasound pulse (20) in a different second direction ($\varphi$) into an object (O) to be imaged, so that said first ultrasound pulse (10) is backscattered in said object towards said ultrasound probe (1) in the form of first ultrasound pulse echoes (11), and so that said second ultrasound pulse (20) is backscattered in said object towards said ultrasound probe (1) in the form of second ultrasound pulse echoes (21),
detecting said backscattered first ultrasound pulse echoes (11) and said backscattered second ultrasound pulse echoes (21) with said ultrasound probe (1),
reconstructing from said detected backscattered first ultrasound pulse echoes (11) a first image of first local echoes (5) and from said detected backscattered second ultrasound pulse echoes (21) a second image of second local echoes (7), wherein said images lie in an image plane spanned by said directions ($\varphi_0, \varphi$),
determining from said reconstructed images the respective resulting local echo phase shift $\Delta\tau(x,z,\varphi,\varphi_0)$ corresponding to the difference in echo time (t) between the respective first local echo and the corresponding second local echo compared to the case of an assumed constant sound speed in said object (O), and determining the local sound speed c(x,z) in said object (O) for at least a region of said image plane in said object (O) from said local echo phase shift $\Delta\tau(x,z,\varphi,\varphi_0)$.

2. Method according to claim 1, characterized in that a sound speed image is generated from the local sound speed c(x,z).

3. Method according to claim 1, characterized in that said determining of the local sound speed c(x,z), said generating of said sound speed image from the local sound speed c(x,z), and/or said visualizing is conducted in real-time.

4. Method according to claim 1, characterized in that the first local echoes (5) of each A-line of said reconstructed first image are modeled as first amplitude-modulated complex sinusoidal carriers, respectively, and that the second local echoes (7) of each A-line of said reconstructed second image are modeled as second amplitude-modulated complex sinusoidal carriers, respectively, wherein the respective local echo phase shift $\Delta\tau(x,z,\varphi,\varphi_0)$ is determined as the phase shift between the respective first carrier and the corresponding second carrier.

5. Method according to claim 1, characterized in that the respective local echo phase shift $\Delta\tau(x,z,\varphi,\varphi_0)$ is determined by
calculating a first Hilbert transform of said first image of first local echoes (5) and a second Hilbert transform of said second image of second local echoes (7), respectively,
calculating a pointwise product between the first Hilbert transform and the complex conjugate of the second Hilbert transform,
calculating a convolution of the point-wise absolute magnitude of the pointwise product with a convolution kernel yielding a local average echo power,
determining a pointwise quotient between the point-wise product and its associated average local echo power,
calculating a complex local average of the point-wise quotient by calculating a convolution of the point-wise quotient with a convolution kernel, and
determining the respective local echo phase shift $\Delta\tau(x,z,\varphi,\varphi_0)$ as the argument of said complex local average of the pointwise quotient.

6. Method according to claim 1, characterized in that the discrete Fourier Transform $\Delta\tau(k_x,k_z,\varphi,\varphi_0)$ of the local echo phase shift $\Delta\tau(x,z,\varphi,\varphi_0)$ is calculated for determining the local sound speed c(x,z).

7. Method according to claim 1 characterized in that the local sound speed c(x,z) in said object is determined from the Fourier transformed local echo phase shift $\Delta\tau(k_x,k_z,\varphi,\varphi_0)$ using the relation $$\sigma(k_x,k_z) = T_{inv}(k_x',k_z',k_x,k_z,\varphi,\varphi_0) \cdot \Delta\tau(k_x',k_z',\varphi,\varphi_0),$$

or a relation equivalent hereto, wherein $\sigma(k_x,k_z)$ is the discrete Fourier transform of the slowness $\sigma(x,z)$, wherein the slowness $\sigma(x,z)$ is the reciprocal of the sound speed c(x,z) minus an average slowness, and $T_{inv}$ is a matrix.

8. Method according to claim 7, characterized in that said matrix $T_{inv}$ is an inverse matrix of the matrix $$T(k_x',k_z',k_x,k_z,\varphi,\varphi_0) = M(k_x',k_z',k_x,k_z,\varphi) - M(k_x',k_z',k_x,k_z,\varphi_0),\ M \text{ having the components } M_{k',k}(\varphi)$$

$$M_{k',k}(\varphi) = \frac{\sqrt{1+\tan^2\varphi}}{i(k_x\tan\varphi + k_z)} \cdot X \cdot \delta(k_x - k_x') \cdot \ldots$$

-continued $$\left\{ Z \cdot \delta(k_z - k_z') + \frac{1}{i(k_x\tan\varphi + k_z')}\{\exp[-i(k_x\tan\varphi + k_z')Z] - 1\} \right\}$$

9. Method according to claim 8, characterized in that said matrix $T_{inv}$ is calculated as the Tikhonov pseudo-inverse matrix:

$$T^{-1} = (T^*T + \Gamma^*\Gamma)^{-1}T^*,$$

wherein * denotes the complex transpose, and $\Gamma$ is a regularising term.

10. Method according to claim 1, characterized in that the slowness $\sigma(x,z)$ is determined from the local echo phase shift $\Delta\tau(x,z,\varphi,\varphi_0)$ iteratively.

11. Method according to claim 1, characterized in that the first direction is specified by a first angle $(\varphi_0)$ which is enclosed by the first direction and an axis (z) that lies in said image plane and extends in a depth direction of the object (O) to be imaged, and wherein said second direction is specified by an angle $(\varphi)$ which is enclosed by the second direction and said axis (z).

12. Method according to claim 1, characterized in that said object (O) is
soft tissue of a human or an animal,
a liver of a human or an animal, or
a part of a human or animal body comprising a tumor.

13. Method according to claim 1, characterized in that at least one of the following further steps are performed:
a temporal evolution of a spatial distribution of the temperature inside the object is determined, using the distribution of the sound speed c(x,z), and a predetermined relation between temperature and sound speed,
an ultrasound image of the object (O) is reconstructed using the determined distribution of the sound speed c(x,z).

14. System for determining sound speed in an object by means of ultrasound, comprising:
an ultrasound probe (1) being designed to transmit at least a first ultrasound pulse (10) in a first direction $(\varphi_0)$ and a second ultrasound pulse (20) in a different second direction $(\varphi)$ into an object (O) to be imaged, so that said first ultrasound pulse (10) is backscattered in said object (O) towards said ultrasound probe (1) in the form of first ultrasound pulse echoes (11), and so that said second ultrasound pulse (20) is backscattered in said object (O) towards said ultrasound probe (1) in the form of second ultrasound pulse echoes (21), wherein said ultrasound probe (1) is further designed to detect said backscattered first ultrasound pulse echoes (11) and said backscattered second ultrasound pulse echoes (21), and
an analyzing means being designed to reconstruct from said detected backscattered first ultrasound pulse echoes (11) a first image of first local echoes (5) and from said detected backscattered second ultrasound pulse echoes (21) a second image of second local echoes (7), wherein said images lie in an image plane spanned by said directions $(\varphi_0,\varphi)$, and to determine from said reconstructed images the respective resulting local echo phase shift $\Delta\tau(x,z,\varphi,\varphi_0)$ corresponding to the difference in echo time (t) between the respective first local echo (5) and the corresponding second local echo (7), relative to the case of an assumed constant sound speed, wherein said analyzing means is further designed to determine the local sound speed $c(x,z)$ in said object for at least a region of said image plane in said object from the local echo phase shift $\Delta\tau(x,z,\varphi,\varphi_0)$.

\* \* \* \* \*